US009643917B2

(12) United States Patent
Li et al.

(10) Patent No.: US 9,643,917 B2
(45) Date of Patent: May 9, 2017

(54) WATER-SOLUBLE PROPOFOL DERIVATIVES AND USES THEREOF

(71) Applicant: JIANGSU NHWALUOKANG PHARMCEUTICAL RESEARCH AND DEVELOPMENT CO., LTD, Xuzhou, Jiangsu (CN)

(72) Inventors: Qingeng Li, Chongqing (CN); Tao Wang, Chongqing (CN); Tong Wu, Chongqing (CN); Lingguo Zeng, Chongqing (CN); Yuanzhong Wang, Chongqing (CN); Wei Mao, Chongqing (CN); Gang Chen, Chongqing (CN)

(73) Assignee: JIANGSU NHWALUOKANG PHARMCEUTICAL RESEARCH AND DEVELOPMENT CO., LTD, Xuzhou (CN)

( * ) Notice: Subject to any disclaimer, the term of this patent is extended or adjusted under 35 U.S.C. 154(b) by 0 days.

(21) Appl. No.: 15/119,596

(22) PCT Filed: Feb. 16, 2015

(86) PCT No.: PCT/CN2015/073171
§ 371 (c)(1),
(2) Date: Aug. 17, 2016

(87) PCT Pub. No.: WO2015/120821
PCT Pub. Date: Aug. 20, 2015

(65) Prior Publication Data
US 2017/0050920 A1    Feb. 23, 2017

(30) Foreign Application Priority Data

Feb. 17, 2014 (CN) ............................ 2014 1 0053129
Feb. 17, 2014 (CN) ............................ 2014 1 0053877
(Continued)

(51) Int. Cl.
*C07C 229/20* (2006.01)
*C07D 295/15* (2006.01)
(Continued)

(52) U.S. Cl.
CPC ............ *C07C 229/20* (2013.01); *C07C 69/67* (2013.01); *C07D 203/08* (2013.01); *C07D 295/15* (2013.01); *C07F 9/145* (2013.01)

(58) Field of Classification Search
CPC combination set(s) only.
See application file for complete search history.

(56) References Cited

U.S. PATENT DOCUMENTS 8,173,840 B2 *    5/2012    Chandran ............ A61K 38/12
562/444

FOREIGN PATENT DOCUMENTS

| CN | 1744908 A | 3/2006 | |
|---|---|---|---|
| CN | 1907954 A | 2/2007 | |
| CN | 101313890 A | 12/2008 | |
| CN | 102020574 A | 4/2011 | |
| WO | WO-9958555 A2 | 11/1999 | |
| WO | WO-2005023204 A2 | 3/2005 | |
| WO | WO 2006017351 A1 * | 2/2006 | ............ C07C 229/22 |

OTHER PUBLICATIONS

"International Application No. PCT/CN2015/073171, International Search Report mailed May 21, 2015", w/ English Translation, (May 21, 2015), 7 pgs.

(Continued)

*Primary Examiner* — Michael Barker
*Assistant Examiner* — Amanda L Aguirre
(74) *Attorney, Agent, or Firm* — Schwegman Lundberg & Woessner, P.A.

(57) ABSTRACT

The present invention discloses a class of water-soluble propofol derivatives, preparation method thereof, anesthetization method using the same, use thereof as prodrugs and use thereof in the preparation of intravenous anesthetics. The water-soluble propofol derivatives have the general formula (I); wherein X is H or F, Y is F or alkyl substituted by one or more F, n is 1, 2, 3, 4, 5 or 6, W is $W^1$ or $W^2$; $W^1$ is $NR^1R^2 \cdot A$ or $$\underset{A}{\overset{}{N}}\hspace{-2pt}\diamondsuit\hspace{-2pt})_m;$$

$R^1$ and $R^2$ are each independently H, alkyl optionally substituted with phenyl, or cycloalkyl, m is 0, 1, 2 or 3, A is a pharmaceutically acceptable acid, $W^2$ is $COOM_{1/t}$ or $OPO_3(M)_{2/t}$ or $PO_3(M)_{2/t}$; M is a metal ion, an ammonium ion or a basic amino acid cation which can form a salt with an acid radical; t is the charge number of M.

(I)

29 Claims, No Drawings

(30) Foreign Application Priority Data

Apr. 17, 2014 (CN) .......................... 2014 1 0154956
Apr. 17, 2014 (CN) .......................... 2014 1 0154994

(51) Int. Cl.
*C07C 69/67* (2006.01)
*C07D 203/08* (2006.01)
*C07F 9/145* (2006.01)
*A61K 31/222* (2006.01)
*A61K 31/225* (2006.01)
*A61K 31/40* (2006.01)
*A61K 31/661* (2006.01)

(56) References Cited

OTHER PUBLICATIONS

"International Application No. PCT/CN2015/073171, Written Opinion mailed May 21, 2015", (May 21, 2015), 4 pgs.

* cited by examiner

WATER-SOLUBLE PROPOFOL DERIVATIVES AND USES THEREOF

CROSS-REFERENCE TO RELATED APPLICATIONS

The present application is a U.S. National Stage Filing under 35 U.S.C. 371 from International Application No. PCT/CN2015/073171, filed on Feb. 16, 2015, and published as WO 2015/120821 on Aug. 20, 2015, which claims the benefit of priority from Chinese patent applications Nos. 201410053129.9 and 201410053877.7 filed on Feb. 17, 2014, and Chinese patent applications Nos. 201410154956.7 and 201410154994.2 filed on Apr. 17, 2014, the contents of which are incorporated herein by reference.

TECHNICAL FIELD

The present invention relates to the field of pharmacy, specifically to water soluble propofol derivatives, anesthetization method using the same, use thereof as prodrugs and use thereof in the preparation of intravenous anesthetics.

BACKGROUND ART

A prodrug, also referred to as a precursor of a drug, refers to a compound which achieves pharmacological action after the conversion in an organism. A prodrug per se has no or little bioactivity, and releases an active agent after metabolism in vivo. The purpose of investigating and preparing a prodrug is to increase the bioavailability, modify the solubility, enhance the targeting properties, or reduce the toxicity or side effects of the parent drug. It is advantageous for many drugs, especially those having low bioavailability, poor water solubility or high toxic side effects, to be prepared into prodrugs. In general, it is required in clinic that a prodrug can be quickly dissociated into a ligand and a parent drug after entering the body, and the ligand is non-toxic. The parent drug thus released can exert pharmaceutical effects, and the non-toxic ligand is of no harm to the body.

Propofol (i.e., 2,6-diisopropylphenol, also referred to as propofolum) is a short-acting intravenous general anesthetic, having the advantages of rapid onset, no clear accumulation, and rapid and complete recovery. An injection of propofol is used to induce and maintain general anesthesia in clinic.

Despite the excellent anaesthetic effect, propofol is difficult to be formulated as a suitable preparation due to its poor water solubility, and thus it has to be administered as an emulsion via injection in clinic. In view of the above, the propofol preparations currently available have the following disadvantages: 1) they have poor physical stability; 2) they may cause vascular embolization due to large oil drop; 3) they will induce pain in patients due to injection; 4) they can only be mixed with a few injectable products before administration; 5) bacteria tend to grow in an emulsion; and 6) they may cause cardiac toxic and side effects, etc. The application of propofol in clinic is highly limited by these disadvantages.

As such, pharmacists have been trying to eliminate these disadvantages by structural modification, so as to obtain a prodrug having good water solubility while maintaining the anesthetic effect of propofol (see International Journal of Pharmaceutics, 1998, 175:195-204; WO9958555; CN1907954A; and CN102020574).

Among the prodrugs of propofol investigated thus far, the most successful one is Fospropofol reported by Stella et al. (see Water-Soluble Prodrugs of Hindered Alcohols, U.S. Pat. No. 6,451,776). This drug, which is administered via endoscope, is marked by Eisai in 2009. However, hydrolysis of fospropofol in vivo results in not only release of propofol but also production of formaldehyde, which has high toxicity. As such, it was pulled out the market not long after being marketed.

SUMMARY OF THE INVENTION

In a first aspect, the present invention provides a carboxylic acid derivative or salt thereof useful as a ligand for the preparation of a water soluble propofol prodrug which has good water solubility and can be quickly dissociated in vivo to release the parent drug, so as to exert effects.

The carboxylic acid derivative of the present invention has following general formula (III):

$$W'(CH_2)_n\overset{\overset{X}{|}}{\underset{\underset{Y}{|}}{C}}COD \quad (III)$$

wherein,
X is H or F;
Y is F or alkyl substituted with one or more F;
n is 1, 2, 3, 4, 5 or 6;
W' is $NR^{1'}R^{2'}$, $NR^{1'}R^{2'}\cdot B$,

[structures: $N\underset{}{\overset{}{\diamondsuit}})_m$, $N\underset{B}{\overset{}{\diamondsuit}})_m$]

$COOR^7$, $OPO(OR^7)_2$ or $PO(OR^7)_2$;
$R^{1'}$, $R^{2'}$ are each independently H, alkyl, cycloalkyl, or a protecting group for amino;
m is 0, 1, 2 or 3;
B is an acid;
$R^7$ is H, or a protecting group for carboxyl or hydroxyl in phosphoric acid;
D is hydroxyl, Cl or Br.

According to an embodiment of the present invention, Y is F or $C_{1-6}$ alkyl substituted with one or more fluorine atoms. Preferably, Y is F, $CF_3$ or $CHF_2$.

According to an embodiment of the present invention, $R^{1'}$ and/or $R^{2'}$ are each independently $C_{1-6}$ alkyl, such as methyl, ethyl, propyl, isopropyl, butyl or isobutyl.

According to an embodiment of the present invention, $R^{1'}$ and/or $R^{2'}$ are each independently $C_{3-6}$ cycloalkyl, such as cyclopropyl, cyclobutyl, cyclopentyl or cyclohexyl.

According to an embodiment of the present invention, $R^{1'}$ and/or $R^{2'}$ are each independently $C_{1-6}$ alkoxycarbonyl optionally substituted with phenyl, such as benzyloxycarbonyl or tert-butyloxycarbonyl.

According to an embodiment of the present invention, $R^{1'}$ and/or $R^{2'}$ are each independently benzyl.

According to an embodiment of the present invention, $R^{1'}$, $R^{2'}$ are each independently H, methyl, ethyl, propyl, isopropyl, butyl, isobutyl, cyclopropyl, cyclobutyl, cyclopentyl, cyclohexyl, benzyloxycarbonyl, tert-butyloxycarbonyl or benzyl.

According to an embodiment of the present invention, the acid B is an acid which can form a salt with amine, such as hydrochloric acid, hydrobromic acid, sulfuric acid, phosphoric acid, trifluoroacetic acid, difluoroacetic acid, fluoroacetic acid, acetic acid, benzensulfonic acid or p-toluene sulfonic acid.

According to an embodiment of the present invention, $R^7$ is $C_{1-6}$ alkyl optionally substituted with one or more phenyls, such as methyl, ethyl, diphenylmethyl, triphenylmethyl or benzyl.

According to an embodiment of the present invention, when X and Y are different (i.e., the α-C of the carboxyl in the carboxylic acid derivative is a chiral atom), the carbon atom to which both X and Y are attached is in a single R configuration, in a single S configuration, or in both R and S configurations.

According to an embodiment of the present invention, the carboxylic acid derivative of the present invention is selected from the group consisting of:

4-N,N-dimethylamino-2-(R)-fluorobutyric acid hydrochloride;
4-N-isopropylamino-2-(R,S)-fluorobutyric acid hydrochloride;
4-N,N-diethylamino-2-(R,S)-trifluoromethylbutyric acid hydrochloride;
4-N-benzylamino-2,2-difluorobutyric acid hydrochloride;
4-N-isobutylamino-2-(R,S)-difluoromethylbutyric acid hydrochloride;
4-N-(aziridin-1-yl)-2-(R,S)-difluoromethylbutyric acid hydrochloride;
4-N-(pyrrolidin-1-yl)-2-(R,S)-fluorobutyric acid hydrochloride;
3-N-benzylamino-2-(R,S)-(1,1-difluoromethyl)propionic acid hydrochloride;
6-N-cyclohexylamino-2-(R,S)-trifluoromethylhexanoic acid hydrochloride;
4-benzyloxy-4-oxo-2-(R,S)-fluorobutyric acid;
5-benzyloxy-5-oxo-2-(R)-fluoropentanoic acid;
6-benzyloxy-6-oxo-2-(S)-fluorohexanoic acid;
dibenzyl[1-(3-(R,S)-fluoro-3-carboxy)propyl] phosphate triester;
dibenzyl[1-(5-(S)-fluoro-5-carboxy)pentyl] phosphate triester;
4-(dibenzyloxy)phosphoryl-2-(R,S)-fluorobutyric acid;
5-(dibenzyloxy)phosphoryl-2-(R)-fluoropentanoic acid;
4-benzyloxy-4-oxo-2-(R,S)-fluorobutyryl chloride;
sodium 5-benzyloxy-5-oxo-2-(R)-fluorovalerate;
dibenzyl[1-(3-(R,S)-fluoro-4-oxo-4-chloro)butyl] phosphate triester;
dibenzyl[potassium 1-(4-(S)-fluoro-5-carboxylate)pentyl] phosphate triester;
4-(dibenzyloxy)phosphoryl-2-(R,S)-fluorobutyryl chloride;
sodium 4-N,N-dimethylamino-2-(R,S)-fluorobutyrate;
calcium 4-N,N-diethylamino-2-(R,S)-fluorobutyrate;
aluminum 3-N-benzylamino-2-(R,S)-benzyloxypropionate;
4-N,N-dimethylamino-2-(R,S)-fluorobutyryl chloride hydrochloride;
4-N-benzylamino-2,2-difluorobutyryl chloride hydrochloride;
4-N,N-dimethylamino-2-(R,S)-fluorobutyric acid; and
4-N,N-dimethylamino-2-(S)-fluorobutyric acid hydrochloride.

In a second aspect, the present invention provides a water soluble propofol derivative. The propofol derivative has stable chemical properties and good water solubility, and can be dissociated quickly in blood plasma to release propofol, so as to quickly exert an anesthestic effect in vivo. Thus, the propofol derivative of the present invention is a very suitable prodrug for a propofol drug.

The water soluble propofol derivative of the present invention has following general formula (I):

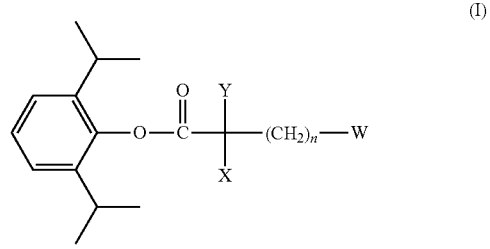

(I)

wherein,

X, Y and n are as defined above for the compound of general formula (III);

W is $W^1$ or $W^2$;

$W^1$ is $NR^1R^2 \cdot A$ or

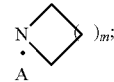

$R^1$, $R^2$ are each independently H, alkyl optionally substituted with phenyl, or cycloalkyl;

m is as defined above for the compound of general formula (III);

A is a pharmaceutically acceptable acid;

$W^2$ is $COOM_{1/t}$ or $OPO_3(M)_{2/t}$ or $PO_3(M)_{2/t}$;

M is a metal ion, an ammonium ion or a basic amino acid cation which can form a salt with an acid radical; and t is the charge number of M.

According to an embodiment of the present invention, W is $W^1$.

According to an embodiment of the present invention, $R^1$ and/or $R^2$ are each independently $C_{1-6}$ alkyl optionally substituted with phenyl, such as methyl, ethyl, propyl, isopropyl, butyl, isobutyl or benzyl.

According to an embodiment of the present invention, $R^1$ and/or $R^2$ are each independently $C_{3-6}$ cycloalkyl, such as cyclopropyl, cyclobutyl, cyclopentyl or cyclohexyl.

According to an embodiment of the present invention, $R^1$, $R^2$ are each independently H, methyl, ethyl, propyl, isopropyl, butyl, isobutyl, benzyl, cyclopropyl, cyclobutyl, cyclopentyl or cyclohexyl.

According to an embodiment of the present invention, $R^1$, $R^2$ are not H at the same time.

According to an embodiment of the present invention, A is hydrochloric acid, hydrobromic acid, sulfuric acid, phosphoric acid, carbonic acid, acetic acid, propionic acid, methanesulfonic acid, lactic acid, benzensulfonic acid, p-toluene sulfonic acid, succinic acid, maleic acid, fumaric acid, tartaric acid, citric acid or malic acid.

According to an embodiment of the present invention, W is $W^2$.

According to an embodiment of the present invention, M is an alkali metal ion, such as a lithium ion, a sodium ion or a potassium ion, an alkaline earth metal ion, such as a magnesium ion, zinc ion or calcium ion, or a trivalent metal ion, such as an aluminum ion.

According to an embodiment of the present invention, M is an ammonium ion represented by formula $(NR^3R^4R^5R^6)^+$ or

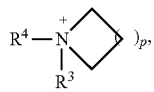

wherein $R^3$, $R^4$, $R^5$, $R^6$ are each independently H, alkyl optionally substituted with phenyl, or cycloalkyl; and p is 0, 1, 2 or 3. Preferably, $R^3$, $R^4$, $R^5$, $R^6$ are each independently H, $C_{1-6}$ alkyl optionally substituted with phenyl, or $C_{3-6}$ cycloalkyl. More preferably, $R^3$, $R^4$, $R^5$, $R^6$ are each independently H, methyl, ethyl, propyl, isopropyl, butyl, isobutyl, benzyl, cyclopropyl, cyclobutyl, cyclopentyl or cyclohexyl. Most preferably, $R^3$, $R^4$ are each independently H, methyl or ethyl.

According to an embodiment of the present invention, M is arginine+$H^+$, lysine+$H^+$ or histidine+$Br^+$.

According to an embodiment of the present invention, the water soluble propofol derivative has following general formula (I-1):

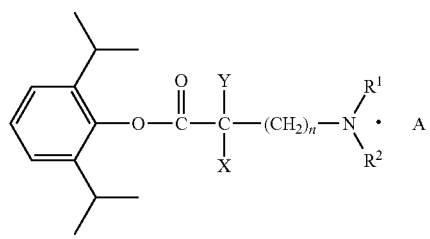

(I-1)

wherein,

X, Y, n, $R^1$, $R^2$ and A are as defined above for the compound of general formula (I).

According to an embodiment of the present invention, the water soluble propofol derivative has following general formula (I-2):

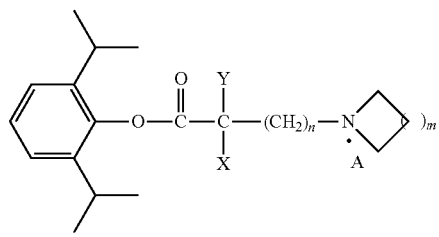

(I-2)

wherein,

X, Y, n, m and A are as defined above for the compound of general formula (I).

According to an embodiment of the present invention, the water soluble propofol derivative has following general formula (I-3):

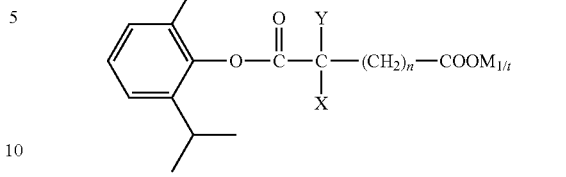

(I-3)

wherein,

X, Y, n, M and t are as defined above for the compound of general formula (I).

According to an embodiment of the present invention, the water soluble propofol derivative has following general formula (I-4):

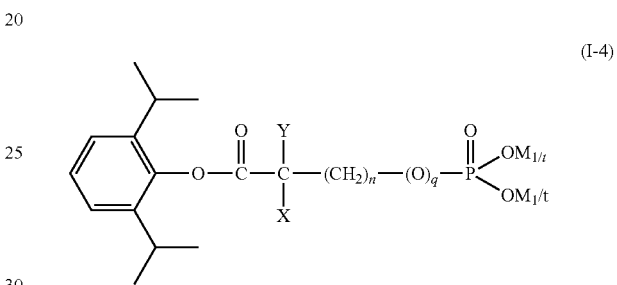

(I-4)

wherein,

X, Y, n, M and t are as defined above for the compound of general formula (I); and q is 0 or 1.

When X and Y are different (i.e., the α-C of carboxyl in a carboxylic acid derivative is a chiral atom), the carbon atom to which both X and Y are attached is in a single R configuration, in a single S configuration, or in both R and S configurations.

According to an embodiment of the present invention, the water soluble propofol derivative is selected from the group consisting of:

propofol 4-(N,N-dimethyl)amino-2-(R,S)-fluorobutyrate hydrochloride;

propofol 4-(N,N-dimethyl)amino-2-(R)-fluorobutyrate hydrochloride;

propofol 3-N-isopropylamino-2-(R,S)-fluoropropionate hydrochloride;

propofol-2-(R,S)-fluoropentanoate monoester sodium salt;

propofol-2-(R,S)-fluorobutyrate monoester sodium salt;

propofol-2-(R)-fluoropropionate monoester sodium salt;

{1-[3-(2,6-diisopropylphenoxy)-3-oxo-2-(R)-fluoropropyl]} phosphate monoester dipotassium salt;

propofol 4-(N,N-dimethyl)amino-2-(R)-fluorobutyrate hydrochloride;

propofol 4-(N,N-dimethyl)amino-2-(R)-2-trifluoromethylbutyrate hydrochloride;

propofol 4-(N-methyl-N-ethyl)amino-2-(R,S)-2-fluorobutyrate hydrochloride;

propofol 5-(N-methyl-N-benzyl)amino-2-(S)-2-fluorovalerate hydrochloride;

propofol 3-(N-isopropyl)amino-2-(R,S)-2-monofluoromethylpropionate methanesulfonate;

propofol 4-(aziridin-1-yl)-2-(S)-2-fluorobutyrate hydrochloride;

propofol 4-(pyrrolidin-1-yl)-2-(R)-2-fluorobutyrate hydrochloride;

propofol 3-(N,N-diethyl)amino-2-(R,S)-fluoropropionate hydrochloride;

propofol 4-(N-methyl-N-benzyl)amino-2-(R,S)-trifluoromethylbutyrate hydrochloride;

propofol 4-(N-cyclopropyl-N-methyl)amino-2-(R)-difluoromethylbutyrate hydrochloride;

propofol 3-(pyrrolidin-1-yl)-2-(S)-trifluoromethyl propionate hydrochloride;

propofol δ-(N,N-dimethyl)amino-2-(R)-fluorovalerate hydrochloride;

propofol 3-N-methyl-N-cyclohexylamino-2-(R,S)-fluoropropionate hydrochloride;

propofol 4-(N-methyl-N-isopropyl)amino-2-(R,S)-fluorobutyrate methanesulfonate;

propofol 5-N-cyclopentylamino-2,2-difluorovalerate hydrochloride;

propofol 4-(N,N-dimethyl)amino-2-(R)-trifluoromethylbutyrate hydrochloride;

propofol 4-N-methyl-N-benzylamino-2-(R)-fluorobutyrate hydrochloride;

propofol 4-carboxyl-2-(S)-fluorovalerate potassium salt;

propofol 4-carboxyl-2-(R)-2-trifluoromethylvalerate lithium salt;

di[propofol 7-carboxyl-2-(R,S)-fluorocaprylate] calcium salt;

di[propofol 5-carboxyl-2-(S)-fluorohexanoate] zinc salt;

tri[propofol 8-carboxyl-2-(R,S)-monofluoromethylpelargonate] aluminum salt;

propofol 4-carboxyl-2-(S)-trifluoromethylbutyrate ammonium salt;

propofol 4-carboxyl-2-(R,S)-difluoromethylvalerate potassium salt;

{1-[4-(2,6-diisopropylphenoxy)-4-oxo-3-(R,S)-3-fluoro-1-butyl]} phosphate monoester dipotassium salt;

{1-[4-(2,6-diisopropylphenoxy)-4-oxo-3-(S)-3-fluoro-1-butyl]} phosphate monoester disodium salt;

{1-[4-(2,6-diisopropylphenoxy)-4-oxo-3-(R)-3-trifluoromethyl-1-butyl]} phosphate monoester dilithium salt;

propofol 4-phosphoryl-2-(R,S)-fluorobutyrate calcium salt;

propofol 5-phosphoryl-2-(S)-fluorovalerate zinc salt;

tri[propofol 3-phosphoryl-2-(R,S)-2-monofluoromethylpropionate] dialuminum salt;

{1-[4-(2,6-diisopropylphenoxy)-4-oxo-2-(R)-trifluoromethylbutyl]} phosphate monoester dilithium salt;

propofol 4-phosphoryl-2-(R)-fluorobutyrate disodium salt; and propofol 3-phosphoryl-2-(R,S)-fluoropropionate zinc salt.

According to the third aspect of the present invention, it provides a water soluble propofol of the present invention for use as intravenous anesthetics.

According to the fourth aspect of the present invention, it provides an anesthetic method, comprising intravenous administration of a water soluble propofol derivative of the present invention to a patient.

According to the fifth aspect of the present invention, it provides use of a water soluble propofol derivative of the present invention in the preparation of an intravenous anesthetic.

DETAILED DESCRIPTION OF THE INVENTION

Definitions

The term "$C_{1-6}$ alkyl" as used herein refers to a saturated, linear or branched hydrocarbon group having 1-6 carbon atoms, such as methyl, ethyl, propyl, isopropyl, n-butyl, isobutyl, sec-butyl, tert-butyl, n-pentyl, isopentyl, neo-pentyl, n-hexyl, isohexyl and the like, preferably methyl, ethyl, propyl, isopropyl, butyl or isobutyl, more preferably methyl, ethyl or propyl.

The term "$C_{3-6}$ cycloalkyl" as used herein refers to a saturated monocyclic hydrocarbon group having 3-6 carbon atoms, such as cyclopropyl, cyclobutyl, cyclopentyl or cyclohexyl.

The term "an protecting group for amino" as used herein refers to a protecting group for preventing an amino group from undergoing undesired chemical reactions, including but not limited to an alkoxycarbonyl protecting group, such as methoxycarbonyl, ethoxycarbonyl, propoxycarbonyl, tert-butyloxycarbonyl, benzyloxycarbonyl and the like, and an alkyl protecting group, such as benzyl with or without substitution on the phenyl ring, and the like.

The term "a protecting group for carboxyl or hydroxyl in phosphoric acid" as used herein refers to a protecting group for preventing a carboxyl or the hydroxyl group in phosphoric acid from undergoing undesired chemical reactions, including but not limited to methyl, ethyl, propyl, diphenylmethyl, triphenylmethyl, benzyl and the like.

The term "an acid which can form a salt with an amine" as used herein refers to an inorganic or organic acid commonly used in the field of organic chemistry which can form a salt with an amine. The inorganic acid includes, but is not limited to, hydrochloric acid, hydrobromic acid, hydroiodic acid, sulfuric acid, pyrosulfuric acid, phosphoric acid, nitric acid and the like. The organic acid includes, but is not limited to, formic acid, acetic acid, propionic acid, butyric acid, pivalic acid, trifluoroacetic acid, difluoroacetic acid, fluoroacetic acid, acetoacetic acid, benzoic acid, methanesulfonic acid, ethanesulfonic acid, trifluoromethanesulfonic acid, benzensulfonic acid, p-toluene sulfonic acid, naphthalenesulfonic acid, camphorsulfonic acid, and the like.

The term "pharmaceutically acceptable acid" as used herein refers to an acid which can be used in the medical field, such as hydrochloric acid, hydrobromic acid, sulfuric acid, phosphoric acid, carbonic acid, acetic acid, propionic acid, methanesulfonic acid, lactic acid, benzensulfonic acid, p-toluene sulfonic acid, succinic acid, maleic acid, fumaric acid, tartaric acid, citric acid or malic acid.

The term "$C_{1-6}$ alkoxycarbonyl" as used herein refers to an alkoxy group linked to the remainder of a molecule via a carbonyl having 1-6 carbon atoms in total, such as methoxycarbonyl, ethoxycarbonyl, propoxycarbonyl, tert-butyloxycarbonyl, pentyloxycarbonyl, etc.

The term "basic amino acid" as used herein refers to an amino acid which results in more hydroxyl anion than hydrogen cation after hydrolysis, such as arginine+$H^+$, lysine+$H^+$ or histidine+$H^+$.

Reaction Scheme

The water soluble propofol derivative of general formula (I) of the present invention can be prepared according to following Reaction Scheme 1:

Reaction Scheme 1

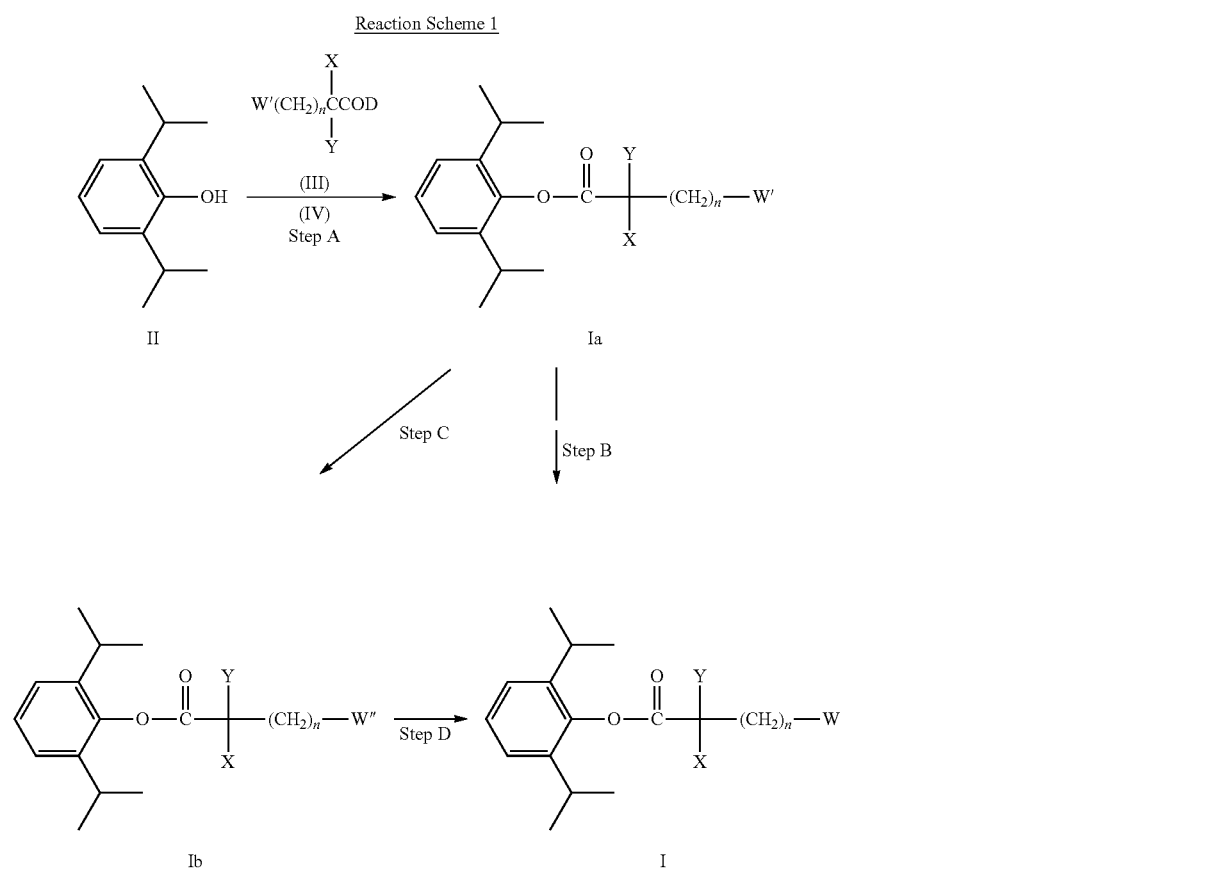

Step A:

The compound of general formula (Ia) is prepared by reacting the compound of formula (II) with the compound of formula (III) (wherein the variables are each as defined as in the section of "Summary of the Invention") in the presence of reagent (IV) in an organic solvent at −100-40° C.

The reagent (IV) is a nitrogen-containing basic organic reagent or a mixed reagent consisting of a nitrogen-containing basic organic reagent and a compound having a carbodiimide structure. The nitrogen-containing basic organic reagent is an organic base, such as triethylamine, pyridine, 4-N,N-dimethylaminopyridine or 4-PPY (4-pyrrolidinylpyridine), and the compound having a carbodiimide structure is DCC (dicyclohexylcarbodiimide) or EDC (1-(3-dimethylaminopropyl)-3-ethylcarbodiimide).

When D in the compound of general formula (III) is Cl or Br, the reagent (IV) is a nitrogen-containing basic organic reagent, and the molar ratio of the compound of formula (II), the compound of formula (III) and the reagent (IV), i.e., (II):(III):(IV)), is 1:(1-12.0):(1-15.0).

When D in the compound of general formula (III) is OH, the reagent (IV) is a mixed reagent consisting of a nitrogen-containing basic organic reagent and a compound having a carbodiimide structure in a molar ratio of 1:(1-5), and the molar ratio of the compound of formula (II), the compound of formula (III) and the reagent (IV), i.e., (II):(III):(IV)), is 1:(1-12.0):(1-15.0) (wherein the amount of the reagent (IV) is based on the amount of the nitrogen-containing basic organic reagent).

Step B:

When W' in the compound of general formula (Ia) is $NR^1R^{2'}.B$ or

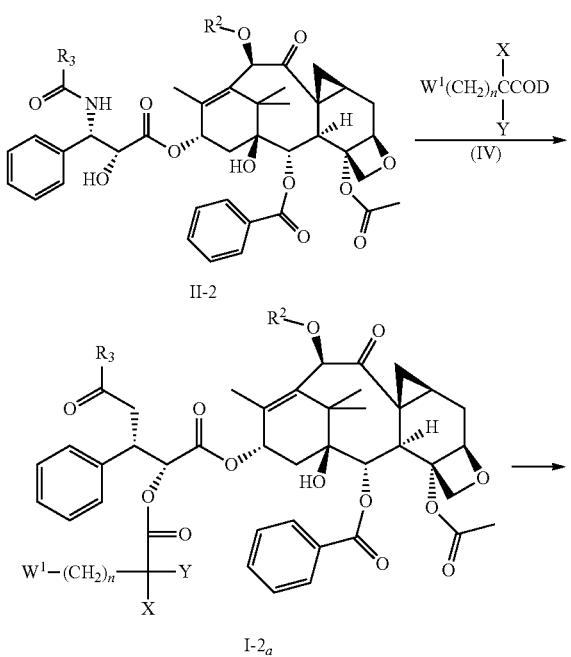

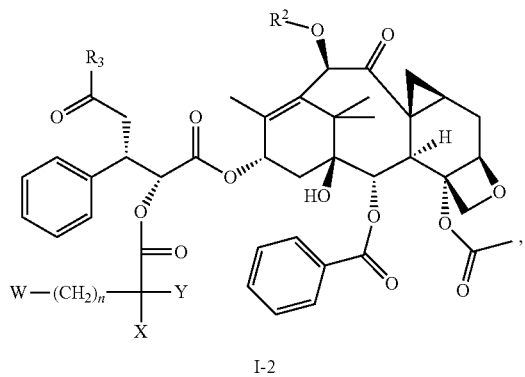

I-2

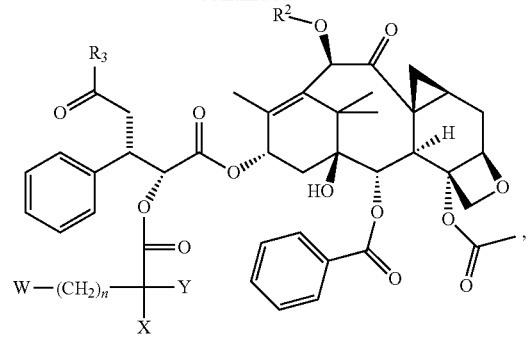

I-2 wherein R¹', R²' are each independently alkyl (especially $C_{1-6}$ alkyl, such as methyl, ethyl, propyl, isopropyl, butyl or isobutyl), cycloalkyl (especially $C_{3-6}$ cycloalkyl, such as cyclopropyl, cyclobutyl, cyclopentyl or cyclohexyl) or benzyl, the compound of general formula (Ia) can be dissolved in an organic solvent, and then the organic layer is washed with a saturated aqueous solution of a salt of acid A which is adjusted to below pH 5 with acid A to obtain a compound of general formula (I).

Step C:

When W' in the compound of general formula (Ia) is $NR^{1'}R^{2'}.B$,

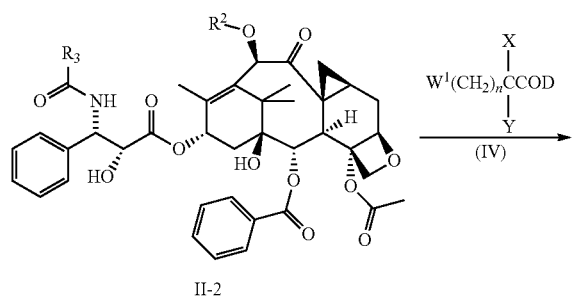

II-2

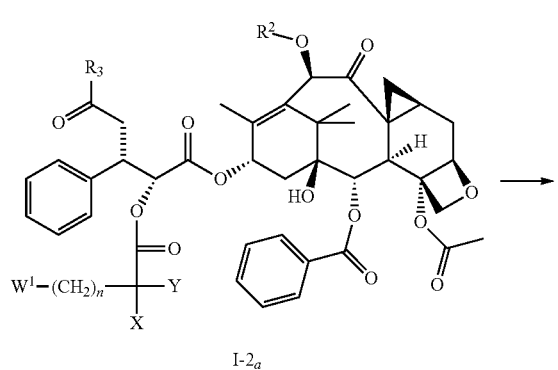

I-2a $COOR^7$, $OPO(OR^7)_2$ or $PO(OR^7)_2$, wherein $R^{1'}$ is hydrogen, alkyl (especially $C_{1-6}$ alkyl, such as methyl, ethyl, propyl, isopropyl, butyl or isobutyl), cycloalkyl (especially $C_{3-6}$ cycloalkyl, such as cyclopropyl, cyclobutyl, cyclopentyl or cyclohexyl) or benzyl, $R^{2'}$ is a protecting group for amino (especially $C_{1-6}$ alkoxycarbonyl optionally substituted with phenyl, such as benzyloxycarbonyl or tert-butyloxycarbonyl or benzyl), and $R^7$ is a protecting group for carboxyl or hydroxyl in phosphoric acid (especially $C_{1-6}$ alkyl optionally substituted with one or more phenyls, such as methyl, ethyl, diphenylmethyl, triphenylmethyl or benzyl), a corresponding deprotection method can be employed to prepare the compound of general formula (Ib) (wherein W" is $NR^1R^2.B$,

$COOH$, $OPO(OH)_2$ or $PO(OH)_2$, and wherein B and m are as defined for the compound of general formula (III) in the section of "Summary of invention").

The deprotection method refers to a conventional method in the art to remove a protecting group for amino acid, carboxyl or the hydroxyl in phosphoric acid.

Step D:

When W" in the compound of general formula (Ib) is $NR^1R^2.B$ or

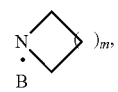

the compound of general formula (Ib) can be dissolved in an organic solvent, and then the organic layer is washed with a saturated aqueous solution of a salt of acid A which is adjusted to below pH 5 with acid A to obtain a compound of general formula (I).

When W" in the compound of general formula (Ib) is COOH, $OPO(OH)_2$ or $PO(OH)_2$, a basic solution containing M ion is added to the compound of general formula (Ib), so as to prepare a compound of general formula (I).

The organic solvent as mentioned above refers to an aprotic organic solvent which can dissolve the compound of general formula (Ia) or the compound of general formula (Ib), e.g., a chlorinated hydrocarbon organic solvent (such as dichloromethane, chloroform, 1,2-dichloroethane, chlorobenzene), an ether organic solvent (such as tetrahydrofuran, dioxane, diethyl ether, methyl ethyl ether), acetonitrile, DMF, DMSO and the like.

The carboxylic acid derivative of general formula (III) of the present invention (i.e., one of the starting materials in Reaction Scheme 1) can be prepared as follows.

When D is OH and W' is $NR^{1'}R^{2'}$, $NR^{1'}R^{2'}\cdot B$,

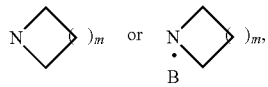

the carboxylic acid derivative of general formula (III) of the present invention can be prepared according to following Reaction Scheme 2:

Reaction Scheme 2

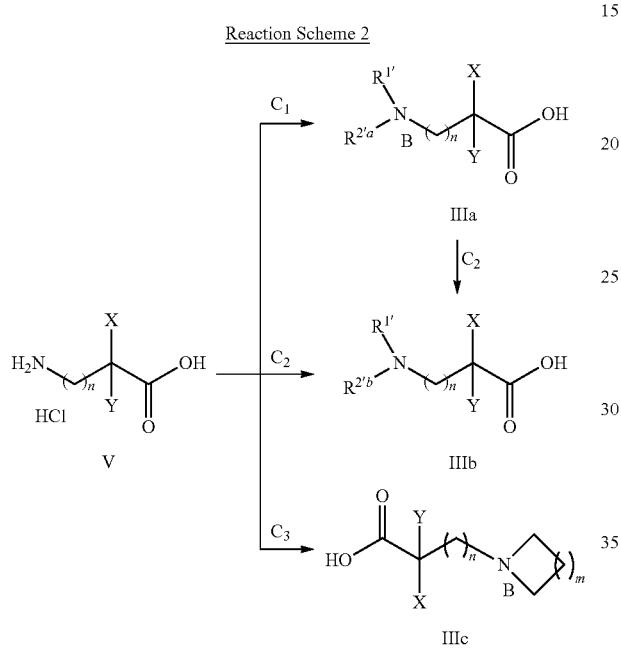

In the above Reaction Scheme 2, the compounds of formulae (IIIa), (IIIb) and (IIIc), which all belong to the compound of general formula (III), are obtained by reacting the compound of general formula (V) with an alkylating agent for amino ($C_1$ or $C_3$) or a protecting reagent for amino ($C_2$), wherein, $R^{1'}$, X, Y, n and B are as defined above;

$C_1$ is an alkylating agent for amino, such as formic acid/formaldehyde, dimethyl sulfate, bromoethane, bromopropane, chlorobutane, acetone, butanone, cyclopentanone, cyclohexanone, benzaldehyde and the like;

$C_2$ is a protecting reagent for amino, such as benzyl chloroformate, di-tert-butyloxycarbonylcarbonic anhydride, benzyl chloride, benzyl bromide and the like;

$C_3$ is another alkylating agent for amino, such as 1-chloro-2-bromoethane, 1-chloro-4-bromobutane, 1-chloro-5-bromopentane and the like;

$R^{2'a}$ is alkyl or cycloalkyl, especially $C_{1-6}$ alkyl, such as methyl, ethyl, propyl, isopropyl, butyl or isobutyl, or $C_{3-6}$ cycloalkyl, such as cyclopropyl, cyclobutyl, cyclopentyl or cyclohexyl.

$R^{2'b}$ is a protecting group for amino, especially $C_{1-6}$ alkoxycarbonyl optionally substituted with phenyl (such as benzyloxycarbonyl or tert-butyloxycarbonyl) or benzyl.

When D is OH and W' is $COOR^7$, $OPO(OR^7)_2$ or $PO(OR^7)_2$, the carboxylic acid derivative of general formula (III) of the present invention can be prepared according to following Reaction Scheme 3:

Reaction Scheme 3

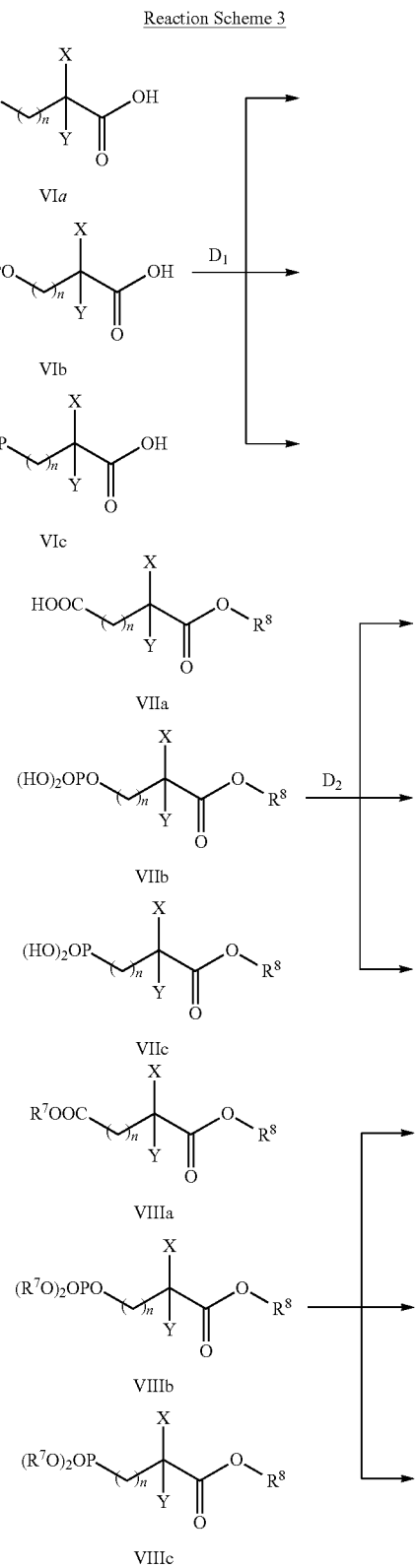

-continued

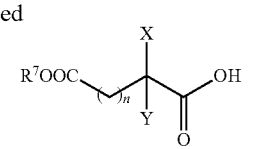

IIIe

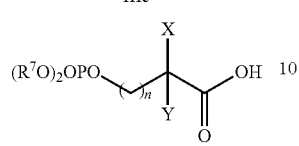

IIIf

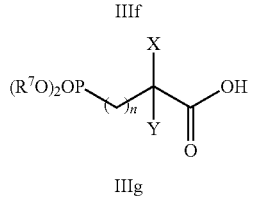

IIIg

In the above Reaction Scheme 3, the compounds of formulae (IIId), (IIIe) and (IIIf), which all belong to the compound of general formula (III), are obtained by the following steps: preparing the compounds of formulae (VIIa), (VIIb) and (VIIc) by reacting the compounds of formulae (VIa), (VIb) and (VIc) with $D_1$ (a protecting agent for the carboxyl at position 1), respectively, then preparing the compounds of formulae (VIIIa), (VIIIb) and (VIIIc) by protecting the terminal carboxyl or the hydroxyl in the phosphoric acid with the protecting agent $D_2$, and finally preparing the compounds of formulae (Id), (Ie) and (If) by removing $R^8$ (the protecting group for the carboxyl at position 1), wherein, $R^7$, X, Y and n are as defined above;

D1, the protecting agent for the carboxyl at position 1, is selected from the group consisting of methanol, methanol substituted with silyl, 9-fluorenylmethanol, 2-iodo-2-methylpropane, benzyl halide and the like;

$D_2$, the protecting agent for the terminal carboxyl or the hydroxyl in the phosphoric acid, is selected from the group consisting of iodomethane, benzophenone hydrazone, triphenylmethyl iodide, benzyl halide and the like;

$R^8$ is a protecting group for the carboxyl group at position 1, such as methyl, alkyl substituted with silyl, 9-fluorenylmethyl, tert-butyl, benzyl and the like.

When D in the compound of formula (III) is Cl or Br, a corresponding acyl halide compound can be prepared from a starting material wherein D is hydroxyl via a halogenating reaction.

The compounds of general formulae (V) and (VI) (including the compounds of general formulae (VIa), (VIb) and (VIc)) in the above reaction schemes can be obtained by methods reported in relevant references, e.g. [1] Chencomm, 1999:1739-1740; [2] J. Med. Chem, 2011, 44:2849-2856; [3] JCS Perkin I 1980:2029-2032, [4] Journal of Fluorine Chemistry (23), 1983:241-259; [5] Journal of Fluorine Chemistry, 2004, vol. 125 (4): 509-515; [6] Phosphorus, Sulfur and Silicon and the Related Elements, 1995, 105 (1-4): 205-212; [7] Tetrahedron Letters, 2007, 48 (4): 711-714; [8] Helvetica Chimica Acta, 1958, 1163, 1167; and [9] Justus Liebigs Annalen der Chemie, 1962, 655:70-80.

Use of the Water Soluble Propofol Derivative of the Present Invention in the Preparation of a General Anesthetic The water soluble propofol of the present invention, as a prodrug, has the following beneficial effects:

According to the present application, the water soluble propofol derivative can be formed through structural modification on the phenolic hydroxyl in propofol without altering the pharmacological activity of the parent drug. The water soluble propofol derivative is relatively stable in chemical properties, and the aqueous solution thereof can release the parent drug to exert an anesthetic effect after injection. In addition, surprisingly, the water soluble propofol derivative of the present invention has good water solubility, can be formulated as a suitable water soluble preparation, and can be easily dissociated in vivo to release propofol. In view of the above advantages, the water soluble propofol derivative of the present invention can overcome the following disadvantages of currently available propofol preparations which have to be administered as an emulsion: they have poor physical stability; they may cause vascular embolization due to large oil drop; they will induce pain in patients due to injection; they can only be mixed with a few injectable products before administration, bacteria tend to grow in an emulsion; and they may cause cardiac toxic and side effects, etc. Also, the water soluble propofol derivative of the present invention has good human compliance and can be easily stored. As demonstrated by pharmacodynamic and pharmacokinetic tests, the water soluble propofol derivative of the present invention has a low toxicity in vivo, and is very suitable as a novel anesthetic.

EXAMPLES

To make the purpose and technical solutions of the present invention more clear, the preferable examples of the present invention are described in detail as follows. It should be noted that the following examples are provided merely for further illustration of the present invention, but should not be construed to limit the scope of the present invention. Any non-essential modifications and/or adjustments to the technical solutions of the present invention by a person skilled in the art based on the above disclosure of the present invention all fall within the protection scope of the present invention.

A. The Preparation of the Carboxylic Acid Derivative of General Formula (III) of the Present Invention Example 1

Preparation of
4-N,N-dimethylamino-2-(R)-fluorobutyric acid hydrochloride 4-amino-2-(R)-fluorobutyric acid hydrochloride (1.1 g, 7.0 mmol) was added to a round bottom flask, a saturated aqueous $Na_2CO_3$ solution was added to adjust the pH value to 8, and then 88% formic acid (6 ml) and 35% aqueous formaldehyde solution (5 ml) were added. The reaction mixture was warmed slowly to 80° C., and was allowed to react for 15 hours. The reaction mixture was cooled to room temperature, and 6 N hydrochloric acid (2 ml) was added followed by concentration under reduced pressure to give a light yellow solid. The solid was dissolved in methanol (10 ml), and the resulting solution was cooled in an ice bath with stirring for 30 min. Then the resulting mixture was filtered, and the filtrate was concentrated. The residue was refluxed in 6 N hydrochloric acid (100 ml) for 4 hours, and the liquid was removed by rotary evaporation. The solid thus obtained was treated with acetonitrile to obtain a white solid (1.1 g, yield: 85%).

m.p.: 136-138° C.;
$^1$H-NMR (400 MHz, $D_2O$): δ 4.72 (ddd, 1H), 2.90 (dtd, 2H), 2.43 (s, 6H), 1.93 (m, 2H);
$^{13}$C-NMR (600 MHz, $D_2O$): δ 173.13, 86.90, 53.49, 42.83, 26.91;
ESI-MS m/z [M+H]$^+$150.13.

Example 2

Preparation of 4-N-isopropylamino-2-(R,S)-fluorobutyric acid hydrochloride 4-amino-2-(R,S)-fluorobutyric acid hydrochloride (1.1 g, 7.0 mmol) was added to a round bottom flask (50 ml), a saturated aqueous $Na_2CO_3$ solution was added to adjust the pH to 8, and then acetone (15 ml) and 5% Pd—C (100 mg) were added. Air was replaced with nitrogen, which was then replaced with hydrogen. The reaction was carried out for 6 hours at room temperature. Pd—C was removed through filtration, and the pH of the solution was adjusted to be acidic with 6 N hydrochloric acid. The solution was concentrated under reduced pressure to give a light yellow solid. The solid was dissolved in methanol (10 ml), and the resulting solution was cooled in an ice bath with stirring for 30 min. Then the resulting mixture was filtered, and the filtrate was concentrated. The residue was refluxed in 6 N hydrochloric acid (100 ml) for 4 hours, and the solvent was removed by rotary evaporation. The solid thus obtained was treated with acetonitrile to obtain a white solid (1.05 g, yield: 75%).

ESI-MS m/z [M+H]$^+$164.12.

Example 3

Preparation of 4-N,N-diethylamino-2-(R,S)-trifluoromethylbutyric acid hydrochloride 4-amino-2-(R,S)-trifluoromethylbutyric acid hydrochloride (2.07 g, 10 mmol) was added to a round bottom flask (50 ml), and 1 N aqueous $NaHCO_3$ solution was added to adjust the pH value to 8, Acetonitrile (50 ml) was added, and a mixed solution (10 ml) of bromoethane (2.18 g, 20 mmol) and acetonitrile was added dropwise. The pH of the reaction solution was maintained at 7-8 with a solution of sodium bicarbonate. Hydrochloric acid was added to adjust the pH to below 5 after completion of the reaction, and the solution was concentrated under reduced pressure to give a light yellow solid. Methanol (10 ml) was added, the resulting solution was stirred for 30 min before filtration, and the filtrate was concentrated. The residue was refluxed in 6 N hydrochloric acid (100 ml) for 4 hours, the solvent was removed by rotary evaporation, and a white solid (yield: 13%) was obtained.

ESI-MS m/z [M+H]$^+$228.16.

Example 4

Preparation of 4-N-benzylamino-2,2-difluorobutyric acid hydrochloride

The title compound was prepared according to the method of Example 2, using 4-amino-2,2-difluorobutyric acid hydrochloride (1.1 g, 5.6 mmol) and benzaldehyde as starting materials.

ESI-MS m/z [M+H]$^+$230.06.

Example 5

Preparation of 4-N-isobutylamino-2-(R,S)-difluoromethylbutyric acid hydrochloride The title compound was prepared according to the method of Example 2, using 4-amino-2-(R,S)-difluoromethylbutyric acid hydrochloride (1.90 g, 10 mmol) and butanone (15 ml) as starting materials, and a white solid (1.1 g, yield: 45%) was obtained.

m.p.: 141-142° C.;
ESI-MS m/z [M+H]$^+$210.1.

Example 6

Preparation of 4-N-(aziridin-1-yl)-2-(R,S)-difluoromethylbutyric acid hydrochloride 4-amino-2-(R,S)-difluoromethylbutyric acid hydrochloride (1.90 g, 10 mmol) was added to a round bottom flask (50 ml), an aqueous $NaHCO_3$ solution was added to adjust the pH to 7-8, and acetonitrile (15 ml) and 1-chloro-2-bromoethane (10 mmol) were added. The reaction was carried out at ambient temperature for 0.5 h, and then the reaction mixture was heated to reflux and was allowed to react under reflux for 2 h. The solvent was removed by evaporation under reduced pressure, and methanol (10 ml) was added to the residue. The resulting solution was then cooled in an ice bath with stirring for 30 min before filtration, and the filtrate was concentrated. The residue was refluxed in 6 N hydrochloric acid (100 ml) for 4 hours, the solvent was removed by rotary evaporation, and a white solid (0.7 g) was obtained.

ESI-MS m/z [M+H]$^+$180.14.

Example 7

Preparation of 4-N-(pyrrolidin-1-yl)-2-(R,S)-fluorobutyric acid hydrochloride

The title compound was prepared according to the method of Example 6, using 4-amino-2-(R,S)-fluorobutyric acid and 1-chloro-4-bromobutane as starting materials.

ESI-MS m/z [M+H]$^+$176.1.

Example 8

Preparation of 3-N-benzylamino-2-(R,S)-(1,1-difluoromethyl)propionic acid hydrochloride The title compound was prepared according to the method of Example 2, using 3-amino-2-(R,S)-(1,1-difluoromethyl) propionic acid hydrochloride and benzaldehyde as starting materials.

ESI-MS m/z [M+H]$^+$230.19.

Example 9

Preparation of 6-N-cyclohexylamino-2-(R,S)-trifluoromethylhexanoic acid hydrochloride The title compound was prepared according to the method of Example 2, using 6-amino-2-(R,S)-trifluoromethylhexanoic acid hydrochloride and cyclohexanone as starting materials.

ESI-MS m/z [M+H]$^+$282.08.

Example 10

Preparation of 4-benzyloxy-4-oxo-2-(R,S)-fluorobutyric acid

At room temperature, 2-(R,S)-fluorosuccinic acid (10 mmol) was dissolved in methanol (30 ml), and the resulting solution was stirred for 2 h. The solvent was removed by evaporation under reduced pressure, and 1-methyl 2-(R,S)-fluorosuccinate was obtained.

ESI-MS m/z [M−H]⁻149.01.

At room temperature, 1-methyl 2-(R,S)-fluorosuccinate (5 mmol) was dissolved in dry dichloromethane (20 ml), and thionyl chloride (0.3 ml) was added. The reaction mixture was heated slowly to reflux, and was allowed to react for 3 h. The remaining thionyl chloride and solvent were removed by evaporation under reduced pressure, and fluorobutyryl chloride was obtained.

Under cooling in an ice bath, a solution of fluorobutyryl chloride (4 mmol) in dichloromethane (5 ml) was added drop wise to a solution of benzyl alcohol (4 mmol) and pyridine (5 mmol) in dichloromethane (10 ml), and the reaction was carried out under ice cooling for 1 h. The organic layer was washed with an aqueous solution of hydrochloric acid (pH 3), and was dried over anhydrous sodium sulfate. The solvent was removed by evaporation under reduced pressure, and methyl 4-benzyloxy-4-oxo-2-(R,S)-fluorobutyrate was obtained.

ESI-MS m/z [M+H]⁺241.18.

Under cooling in an ice bath, methyl 4-benzyloxy-4-oxo-2-(R,S)-fluorobutyrate (7 mmol) was dissolved in methanol (10 ml), 1 N NaOH solution (1 ml) was added, and the reaction was carried out under ice cooling for 1 h. Methanol was removed by evaporation under reduced pressure, water (10 ml) was added, and the pH of the reaction was neutralized to below 1 with 1 N hydrochloric acid. The aqueous layer was extracted with diethyl ether, and the diethyl ether layers were combined, dried over anhydrous sodium sulfate, and filtered. The solvent was removed by evaporation under reduced pressure, and 4-benzyloxy-4-oxo-2-(R,S)-fluorobutyric acid (yield: 40%) was obtained.

ESI-MS m/z [M−H]⁻225.18.

Example 11

Preparation of 5-benzyloxy-5-oxo-2-(R)-fluoroglutaric acid

The title compound was prepared according to the method of Example 10, using 2-(R)-fluoroglutaric acid as a starting material.

ESI-MS m/z [M−H]⁻239.19.

Example 12

Preparation of 6-benzyloxy-6-oxo-2-(S)-fluoropentanoic acid

The title compound was prepared according to the method of Example 10, using 2-(S)-fluoroadipic acid as a starting material.

ESI-MS m/z [M−H]⁻253.17.

Example 13

Preparation of dibenzyl [1-(3-(R,S)-fluoro-3-carboxy)propyl] phosphate triester At room temperature, [1-(3-(R,S)-fluoro-3-carboxy)propyl] phosphate monoester (10 mmol) was dissolved in methanol (10 ml), and the resulting solution was stirred for 1 h. Methanol was removed by evaporation under reduced pressure, and [1-(3-(R,S)-fluoro-4-oxo-4-methoxy)butyl] phosphate monoester was obtained.

ESI-MS m/z [M−H]⁻215.07.

At room temperature, [1-(3-(R,S)-fluoro-4-oxo-4-methoxy)butyl] phosphate monoester (7 mmol) was dissolved in dry acetonitrile (20 ml), anhydrous potassium carbonate (17 mmol) and benzyl bromide (17 mmol) were added, and the reaction mixture was heated slowly to reflux. After completion of the reaction as monitored by TLC, the reaction mixture was cooled and filtered, and the solvent was removed by rotary evaporation. The residue was purified by column chromatography (EA:PE=1:3), and dibenzyl [1-(3-(R,S)-fluoro-4-oxo-4-methoxy)butyl] phosphate triester was obtained.

ESI-MS m/z [M+H]⁺397.08.

Under cooling in an ice bath, dibenzyl [1-(3-(R,S)-fluoro-4-oxo-4-methoxy)butyl] phosphate triester (10 mmol) was dissolved in tetrahydrofuran (10 ml), 1 N NaOH solution (1 ml) was added slowly, and the reaction mixture was stirred under ice cooling for 1 h until a white solid precipitated. The reaction mixture was filtered, the filter cake was dissolved in water (10 ml), and the pH was adjusted to below 1 with concentrated hydrochloric acid. The aqueous layer was extracted with diethyl ether, and the diethyl ether layers were combined and dried over anhydrous sodium sulfate. Diethyl ether was removed by rotary evaporation to obtain the product (yield: 63.5%).

ESI-MS m/z [M−H]⁻381.29.

Example 14

Preparation of dibenzyl [1-(5-(S)-fluoro-5-carboxy)pentyl] phosphate triester The title compound was prepared according to the method of Example 13, using [1-(5-(S)-fluoro-5-carboxy)pentyl] phosphate monoester as a starting material.

ESI-MS m/z [M−H]⁻409.29.

Example 15

Preparation of 4-(dibenzyloxy)phosphoryl-2-(R,S)-fluorobutyric acid

The title compound was prepared according to the method of Example 13, using 4-(dihydroxy)phosphoryl-2-(R,S)-fluorobutyric acid as a starting material.

ESI-MS m/z [M−H]⁻365.28.

Example 16

Preparation of 5-(dibenzyloxy)phosphoryl-2-(R)-fluoropentanoic acid

The title compound was prepared according to the method of Example 13, using 5-(dihydroxy)phosphoryl-2-(R)-fluoropentanoic acid as a starting material.

ESI-MS m/z [M−H]⁻379.31.

According to the methods of the above examples, the inventors also prepared the following compounds:

4-benzyloxy-4-oxo-2-(R,S)-fluorobutyryl chloride (ESI-MS m/z [M−H]245.01);

sodium 5-benzyloxy-5-oxo-2-(R)-fluorovalerate (ESI-MS m/z [M−H]240.05);

dibenzyl [1-(3-(R,S)-fluoro-4-oxo-4-chloro)butyl] phosphate triester (ESI-MS m/z [M−H]401.02);

dibenzyl [potassium 1-(4-(S)-fluoro-5-carboxylate)pentyl] phosphate triester (ESI-MS m/z [M−H]396.01);

4-(dibenzyloxy)phosphoryl-2-(R,S)-fluorobutyryl chloride (ESI-MS m/z [M−H]385.04);

sodium 4-N,N-dimethylamino-2-(R,S)-fluorobutyrate (ESI-MS m/z [M−H]149.03);

calcium 4-N,N-diethylamino-2-(R,S)-fluorobutyrate (ESI-MS m/z [M−H]177.08);

aluminum 3-N-benzylamino-2-(R,S)-benzyloxypropionate (ESI-MS m/z [M−H]197.04);

4-N,N-dimethylamino-2-(R,S)-fluorobutyryl chloride hydrochloride (ESI-MS m/z [M−H]168.01);

4-N-benzylamino-2,2-difluorobutyryl chloride hydrochloride (ESI-MS m/z [M−H]248.03);

4-N,N-dimethylamino-2-(R,S)-fluorobutyric acid (ESI-MS m/z [M−H]150.08); and

4-N,N-dimethylamino-2-(S)-fluorobutyric acid hydrochloride (ESI-MS m/z [M−H]150.11).

B. The Preparation of the Water Soluble Propofol Derivative of the Present Invention

B-1. Amino Acid-Based Propofol Derivatives of Formula (E)

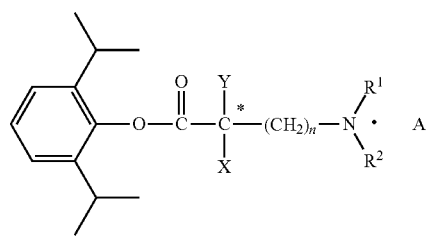

(E)

Example 17

Propofol 4-(N,N-dimethyl)amino-2-(R,S)-fluorobutyrate hydrochloride (E1)

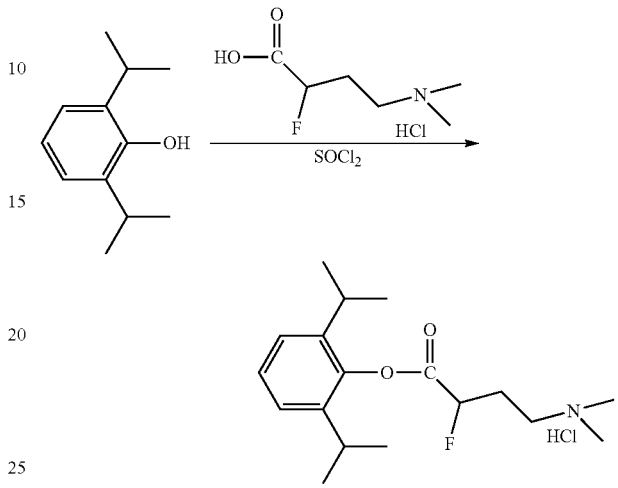

1) Preparation of 4-N,N-dimethylamino-2-(R,S)-fluorobutyryl chloride hydrochloride: 4-N,N-dimethylamino-2-(R,S)-fluorobutyric acid hydrochloride (prepared according to the method of Example 1) (10 mmol) was placed in thionyl chloride (10 ml). The reaction mixture was warmed slowly to 40° C., and was allowed to react for 4 h. Thionyl chloride was removed by evaporation under reduced pressure, anhydrous dichloromethane (DCM, 15 ml) was added, and the solvent was removed by evaporation under reduced pressure after stirring. Anhydrous dichloromethane (60 ml) was added to the residue for the next step.

2) A solution of propofol (4.5 mmol) in dichloromethane (5 ml) was added dropwise to the solution of 4-N,N-dimethylamino-2-(R,S)-fluorobutyryl chloride hydrochloride in dichloromethane prepared in step 1) at −78° C. Then, a solution of 4-N,N-dimethylaminopyridine (8.2 mmol) in dichloromethane (20 ml) was slowly added. The reaction was monitored by HPLC. Upon the reaction was complete, the DCM layer was washed with aqueous hydrochloric acid solution (the pH of which is about 1.0), dried over anhydrous sodium sulfate, and filtered. Most DCM was removed by rotary evaporation, and diethyl ether was slowly added dropwise until a large amount of solid precipitated out. The resulting mixture was frozen for crystallization, filtered and dried to obtain a white solid (yield: 83%).

¹H-NMR (CDCl₃) δ 1.22 (9H, d, Me), 2.10 (3H, m, Me), 2.88 (6H, m, NMe), 3.32 (2H, m, CH₂), 5.43 (1H, m, F—CH), 7.21 (3H, m, Ph);

ESI-MS [M+H]⁺310.1.

Example 18

Propofol 4-(N,N-dimethyl)amino-2-(R)-fluorobutyrate hydrochloride (E2)

At −10° C., E2 was prepared according to the method of Example 17, using 4-N,N-dimethylamino-2-(R)-fluorobutyric acid hydrochloride (10 mmol), propofol (4.5 mmol) and DMAP (10 mmol) as starting materials (yield: 87%, purity: 99.4%).

$^1$H-NMR (CDCl$_3$) δ 1.22 (9H, d, Me), 2.10 (3H, m, Me), 2.88 (6H, m, NMe), 3.32 (2H, m, CH$_2$), 5.43 (1H, m, F—CH), 7.21 (3H, m, Ph);
ESI-MS [M+H]$^+$310.1.

Example 19

Propofol 3-N-isopropylamino-2-(R,S)-fluoropropionate hydrochloride (E19)

1) Preparation of 3-N-isopropylamino-2-(R,S)-fluoropropionic acid: 3-N-isopropylamino-2-(R,S)-fluoropropionic acid hydrochloride (1.0 g) was dissolved in a 1 N NaOH solution (40 ml), tetrahydrofuran (THF, 20 ml) was added, and benzyl chloroformate (Cbz-Cl, 4.5 g) was added dropwise at room temperature for about half an hour. The reaction solution was allowed to react at room temperature for 4 hours with the pH of the reaction solution adjusted to 8-9 with 1 N NaOH during the reaction. THF was removed under reduced pressure, and the aqueous layer was extracted with ethyl acetate (15 ml×3). The aqueous layer was adjusted to pH 3 with hydrochloric acid, and was extracted with diethyl ether (20×3). The diethyl ether layers were combined, dried over anhydrous sodium sulfate, and filtered, and the filtrate was concentrated under reduced pressure to obtain 3-N-Cbz-N-isopropyl amino-2-(R,S)-fluoropropionic acid (1.5 g).

2) Propofol (2.8 mmol) was dissolved in pyridine (1.5 ml), and a solution of 3-N-Cbz-N-isopropylamino-2-(R,S)-fluoropropionyl chloride (prepared according to the method of Example 17.1, using 3-N-Cbz-N-isopropylamino-2-(R,S)-fluoropropionic acid as a starting material) (5 mmol) in dichloromethane (10 ml) was added dropwise under cooling in an ice bath. After addition, the reaction mixture was allowed to react at room temperature for more than 1 h with stirring. After completion of the reaction, a HCl solution was added until the pH reaches about 3. The reaction solution was washed with water to neutral. The organic layer was dried over anhydrous sodium sulfate, and filtered, and the solvent was removed by evaporation under reduced pressure. The residue was purified by column chromatography (silica gel: 200-300 mesh), and the solvent was removed by evaporation under reduced pressure to obtain an oil (0.86 g, yield: 69%).

3) Propofol 3-N-isopropylamino-2-(R,S)-fluoropropionate hydrochloride: propofol (2 g) and 3-N-Cbz-N-isopropylamino-2-(R,S)-fluoropropionate (4.5 mmol) were dissolved in acetic acid (10 ml), 10% Pd—C (0.5 g) was added, and hydrogen was introduced at room temperature for 3 h. After completion of the reaction, water (5 ml) was added, and the mixture was filtered. Solid NaHCO$_3$ was added to the filtrate under cooling in an ice bath until no bubble was produced. The mixture was extracted with diethyl ether (15 ml×3), and the diethyl ether layer was dried over anhydrous sodium sulfate, and filtered. The diethyl ether layer was concentrated to 6 ml. With stirring under cooling in an ice bath, a saturated diethyl ether solution of HCl was added dropwise until a white solid precipitated out. The resulting mixture was filtered, dried under reduced pressure at room temperature, and a white solid (0.81 g, yield: 52%) was obtained.
ESI-MS [M+H]$^+$310.3.

B-2. Diacid Monoester-Based Propofol Derivatives of Formula (F)

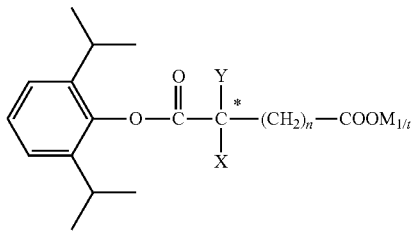

(F)

Example 20

Propofol-2-(R)-fluoropentanoate monoester sodium salt (F1)

5-Benzyloxy-5-oxo-2-(R,S)-fluoropentanoyl chloride (prepared according to Example 17.1, using 5-benzyloxy-5-oxo-2-(R,S)-fluoropentanoic acid as a starting material) (7.2 mmol) was dissolved in dichloromethane (30 ml). In an ice-salt bath at −20° C., a solution of 4-N,N-dimethylaminopyridine (10 mmol) in dichloromethane (20 mmol) was slowly added. Propofol (7 mmol) was added dropwise, and the solution was further stirred at −40° C. After completion of the reaction detected by TLC, the reaction mixture was poured into an aqueous solution of hydrochloric acid (pH 1, 25 ml). The oil layer was separated after fully stirring, washed with an aqueous solution of hydrochloric acid (pH 1, 15 ml), and dried over anhydrous sodium sulfate before filtration. The filtrate was evaporated to dryness, and the product thus obtained was dissolved in anhydrous tetrahydrofuran (45 ml), and subjected to hydrogenolysis under the catalysis of Pd/C. After completion of hydrogenolysis, Pd/C was removed by filtration, and a solution of sodium tert-butoxide (3 mmol) in tert-butanol (15 ml) was slowly added to the filtrate in an ice bath until a solid precipitated out. The precipitated solid was filtered, and the filter cake was washed with a little tetrahydrofuran and dried to obtain propofol-2-(R)-fluoropentanoate monoester sodium salt as a white solid (yield: 48%).
ESI-MS [M−H]$^-$309.14.

Example 21

Propofol-2-(R)-fluorobutyrate monoester sodium salt (F7)

4-Benzyloxy-4-oxo-2-(R,S)-fluorobutyryl chloride (7.2 mmol) was dissolved in dichloromethane (30 ml). In an ice-salt bath at −20° C., a solution of 4-N,N-dimethylaminopyridine (10 mmol) in dichloromethane (20 ml) was slowly added. Propofol (7 mmol) was added dropwise, and the solution was further stirred at −40° C. After completion of the reaction detected by TLC, the reaction mixture was poured into an aqueous solution of hydrochloric acid (pH 1, 25 ml). The oil layer was separated after fully stirring, washed with an aqueous solution of hydrochloric acid (pH 1, 15 ml), and dried over anhydrous sodium sulfate before filtration. The filtrate was evaporated to dryness, and the product thus obtained was dissolved in anhydrous tetrahydrofuran (45 ml), and subjected to hydrogenolysis under the catalysis of Pd/C. After completion of hydrogenolysis, Pd/C was removed by filtration, and a solution of sodium tert-butoxide (3 mmol) in tert-butanol (15 ml) was slowly added to the filtrate in an ice bath until a solid precipitated out. The precipitated solid was filtered, and the filter cake was washed with a little tetrahydrofuran and dried to obtain propofol-2-(R)-fluorobutyrate monoester sodium salt as a white solid (yield: 48%).

ESI-MS [M−H]⁻295.11;

¹H-NMR (400 MHz, CHCl₃) δ 7.34-7.14 (m, 3H), 5.61 (ddd, J=46.9, 7.2, 4.6 Hz, 1H), 3.38-3.13 (m, 2H), 2.90 (dt, J=13.6, 6.8 Hz, 2H), 1.34-1.13 (m, 12H).

Example 22

Propofol-2-(R)-fluoropropionate monoester sodium salt (F8)

3-Benzyloxy-3-oxo-2-(R)-fluoropropionyl chloride (prepared according to Example 17.1, using 3-benzyloxy-3-oxo-2-(R)-fluoropropionic acid as a starting material) (7.2 mmol) was dissolved in dichloromethane (30 ml). In an ice-salt bath at −20° C., a solution of 4-N,N-dimethylaminopyridine (10 mmol) in dichloromethane (20 ml) was slowly added. Propofol (7 mmol) was added dropwise, and the solution was further stirred at −20° C. After completion of the reaction detected by TLC, the reaction mixture was poured into an aqueous solution of hydrochloric acid (pH 1, 25 ml). The oil layer was separated after fully stirring, washed with an aqueous solution of hydrochloric acid (pH 1, 15 ml), and dried over anhydrous sodium sulfate before filtration. The filtrate was evaporated to dryness, and the product thus obtained was dissolved in anhydrous tetrahydrofuran (45 ml), and subjected to hydrogenolysis under the catalysis of Pd/C. After completion of hydrogenolysis, Pd/C was removed by filtration, and a solution of sodium tert-butoxide (3 mmol) in tert-butanol (15 ml) was slowly added to the filtrate in an ice bath until a solid precipitated out. The precipitated solid was filtered, and the filter cake was washed with a little tetrahydrofuran and dried to obtain propofol-2-(R)-fluoropropionate monoester sodium salt as a white solid (yield: 51%).

ESI-MS [M−H]⁻281.09.

B-3. Organic Phosphate-Based Propofol Derivatives of Formula G

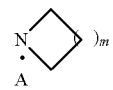

Example 23

{1-[3-(2,6-diisopropylphenoxy)-3-oxo-2-(R)-fluoropropyl]} phosphate monoester dipotassium salt (G7)

At −30° C., dibenzyl {1-[3-(2,6-diisopropylphenoxy)-3-oxo-2-(R)-fluoropropyl]} phosphate triester was prepared according to the method of Example 20, using dibenzyl {1-[3-chloro-3-oxo-2-(R)-fluoropropyl]} phosphate triester (prepared according to example 17.1, using dibenzyl [1-(3-(R)-fluoro-3-carboxy)propyl] phosphate triester (prepared according to example 13) as a starting material) (7 mmol), propofol (5 mmol) and DMAP (10 mmol) as starting materials (yield: 72%).

The compound thus obtained was dissolved in tetrahydrofuran (35 ml), and subjected to hydrogenolysis under the catalysis of Pd/C. After completion of hydrogenolysis detected by TLC, Pd/C was removed by filtration, and a solution of potassium tert-butoxide (4 mmol) in tert-butanol (15 ml) was slowly added to the filtrate in an ice bath until a solid precipitated out. The precipitated solid was filtered, and the filter cake was washed with a little tetrahydrofuran and dried to obtain 1-[3-(2,6-diisopropylphenoxy)-3-oxo-2-(R)-fluoropropyl]} phosphate monoester dipotassium salt as a white solid (yield: 34%).

ESI-MS m/z [M−2K+H]⁺347.24.

The compounds of types E, F and G listed in Table 1 were prepared according to the above examples.

TABLE 1

Water soluble propofol derivatives of types E, F and G

| Compd. No. | Name of target compound | Main starting materials | MS data |
|---|---|---|---|
| E2 | propofol 4-N,N-dimethylamino-2-(R)-fluorobutyrate hydrochloride | 4-N,N-dimethylamino-2-(R)-fluorobutyryl chloride hydrochloride, propofol, DMAP | ESI-MS [M + H]⁺ 310.1 |
| E3 | propofol 4-N,N-dimethylamino-2-(R)-2-trifluoromethylbutyrate hydrochloride | 4-N,N-dimethylamino-2-(R)-2-trifluoromethylbutyryl chloride hydrochloride, propofol, DMAP | ESI-MS [M + H]⁺ 360.18 |
| E4 | propofol 4-N-methyl-N-ethylamino-2-(R,S)-2-fluorobutyrate hydrochloride | 4-N,N-dimethylamino-2-(R)-2-trifluoromethylbutyryl chloride hydrochloride, propofol, DMAP | ESI-MS [M + H]⁺ 324.21 |
| E5 | propofol 5-N-methyl-N-benzylamino-2-(S)-2-fluorovalerate hydrochloride | 5-N-methyl-N-benzylamino-2-(S)-2-fluoropentanoyl chloride hydrochloride, propofol, DMAP | ESI-MS [M + H]⁺ 400.24 |
| E6 | propofol 3-N-isopropylamino-2-(R,S)-2-monofluoromethylpropionate methanesulfonate | 3-N-isopropylamino-2-(R,S)-2-monofluoromethylpropionyl chloride hydrochloride, propofol, DMAP | ESI-MS [M + H]⁺ 324.22 |

TABLE 1-continued

Water soluble propofol derivatives of types E, F and G

| Compd. No. | Name of target compound | Main starting materials | MS data |
|---|---|---|---|
| E7 | propofol 4-(aziridin-1-yl)-2-(S)-2-fluorobutyrate hydrochloride | 4-(aziridin-1-yl)-2-(S)-2-fluorobutyryl chloride hydrochloride, propofol, DMAP | ESI-MS [M + H]+ 308.15 |
| E8 | propofol 4-(pyrrolidin-1-yl)-2-(R)-2-fluorobutyrate hydrochloride | 4-(pyrrolidin-1-yl)-2-(R)-2-fluorobutyryl chloride hydrochloride, propofol, DMAP | ESI-MS [M + H]+ 336.19 |
| E9 | propofol 3-N,N-diethylamino-2-(R,S)-fluoropropionate hydrochloride | 3-N,N-diethylamino-2-(R,S)-fluoropropionyl chloride hydrochloride, propofol, DMAP | ESI-MS [M + H]+ 324.17 |
| E10 | propofol 4-N-methyl-N-benzylamino-2-(R,S)-trifluoromethylbutyrate hydrochloride | 4-N-methyl-N-benzylamino-2-(R,S)-trifluoromethylbutyryl chloride hydrochloride, propofol, DMAP | ESI-MS [M + H]+ 436.18 |
| E11 | propofol 4-N-cyclopropyl-N-methylamino-2-(R)-difluoromethylbutyrate hydrochloride | 4-N-cyclopropyl-N-methylamino-2-(R)-difluoromethylbutyryl chloride hydrochloride, propofol, DMAP | ESI-MS [M + H]+ 368.09 |
| E12 | propofol 3-(pyrrolidin-1-yl)-2-(S)-trifuoromethyl propionate hydrochloride | 3-(pyrrolidin-1-yl)-2-(S)-trifluoromethylpropionyl chloride hydrochloride, propofol, DMAP | ESI-MS [M + H]+ 372.28 |
| E13 | propofol δ-N,N-dimethylamino-2-(R)-fluorovalerate hydrochloride | δ-N,N-dimethylamino-2-(R)-fluoropentanoyl chloride hydrochloride, propofol, 4-PPY | ESI-MS [M + H]+ 324.12 |
| E14 | propofol 3-N-methyl-N-cyclohexylamino-2-(R,S)-fluoropropionate hydrochloride | 3-N-methyl-N-cyclohexylamino-2-(R,S)-fluoropropionyl chloride hydrochloride, propofol, pyridine | ESI-MS [M + H]+ 364.16 |
| E15 | propofol 4-N-methyl-N-isopropylamino-2-(R,S)-fluorobutyrate methanesulfonate | propofol 4-N-methyl-N-isopropylamino-2-(R,S)-fluorobutyrate hydrochloride, sodium methanesulfonate | ESI-MS [M + H]+ 338.18 |
| E16 | propofol 5-N-cyclopentylamino-2,2-difluorovalerate hydrochloride | 5-N-Cbz-N-cyclopentylamino-2,2-difluoropentanoyl chloride, propofol, triethylamine | ESI-MS [M + H]+ 382.15 |
| E17 | propofol 4-N,N-dimethylamino-2-(R)-trifluoromethylbutyrate hydrochloride | 4-N,N-dimethylamino-2-(R)-trifluoromethylbutyric acid hydrochloride, propofol, DMAP | ESI-MS [M + H]+ 360.16 |
| E18 | propofol 4-N-methyl-N-benzylamino-2-(R)-fluorobutyrate hydrochloride | 4-N-methyl-N-benzylamino-2-(R)-fluorobutyric acid hydrochloride, propofol, DMAP, EDCI | ESI-MS [M + H]+ 386.13 |
| F2 | propofol 4-carboxyl-2-(S)-fluorovalerate potassium salt | 2-(S)-fluoro-5-benzyloxy-5-oxo-pentanoyl chloride, propofol, 4-N,N-dimethylaminopyridine | ESI-MS [M − H]− 309.11 |
| F3 | propofol 4-carboxyl-2-(R)-2-trifluoromethyl valerate lithium salt | 2-(R)-trifluoromethyl-5-benzyloxy-5-oxo-pentanoyl chloride, propofol, 4-N,N-dimethylaminopyridine | ESI-MS [M − H]− 359.11 |
| F4 | di[propofol 7-carboxyl-2-(R,S)-fluorocaprylate] calcium salt | 2-(R,S)-fluoro-8-benzyloxy-8-oxo-octanoyl chloride, propofol, 4-N,N-dimethylaminopyridine | ESI-MS [M − H]− 351.14 |
| F5 | di[propofol 5-carboxyl-2-(S)-fluorohexanoate] zinc salt | 2-(S)-fluoro-6-benzyloxy-6-oxo-hexanoyl chloride, propofol, 4-N,N-dimethylaminopyridine | ESI-MS [M − H]− 323.12 |
| F6 | tri[propofol 8-carboxyl-2-(R,S)-monofluoromethylpelargonate] aluminum salt | 2-(R,S)-monofluoromethyl-9-benzyloxy-9-oxo-nonanoyl chloride, propofol, 4-N,N-dimethylaminopyridine | ESI-MS [M − H]− 379.18 |
| F9 | propofol 4-carboxyl-2-(S)-trifluoromethylbutyrate ammonium salt | 2-(S)-trifluoromethyl-4benzyloxy-4-oxo-butyryl chloride, propofol, 4-N,N-dimethylaminopyridine | ESI-MS [M − H]− 345.29 |

TABLE 1-continued

Water soluble propofol derivatives of types E, F and G

| Compd. No. | Name of target compound | Main starting materials | MS data |
|---|---|---|---|
| F10 | propofol 4-carboxyl-2-(R,S)-difluoromethylvalerate potassium salt | 2-(R,S)-difluoromethyl-5-benzyloxy-5-oxo-pentanoyl chloride, propofol, 4-N,N-dimethylaminopyridine | ESI-MS [M − H]− 341.32 |
| G1 | {1-[4-(2,6-diisopropylphenoxy)-4-oxo-3-(R,S)-3-fluoro-1-butyl]} phosphate monoester dipotassium salt | dibenzyl {1-[4-chloro-4-oxo-3-(R,S)-3-fluoro-1-butyl]} phosphate triester, propofol, DMAP | ESI-MS m/z [M − 2K + H]1− 361.13 |
| G2 | {1-[4-(2,6-diisopropylphenoxy)-4-oxo-3-(S)-3-fluoro-1-butyl]} phosphate monoester disodium salt | dibenzyl {1-[4-chloro-4-oxo-3-(S)-3-fluoro-1-butyl]} phosphate triester, propofol, DMAP | ESI-MS m/z [M − 2Na + H]1− 361.13 |
| G3 | {1-[4-(2,6-diisopropylphenoxy)-4-oxo-3-(R)-3-trifluoromethyl-1-butyl]} phosphate monoester dilithium salt | dibenzyl {1-[4-chloro-4-oxo-3-(R)-3-trifluoromethyl-1-butyl]} phosphate triester, propofol, DMAP | ESI-MS m/z [M − 2Li + H]1− 411.13 |
| G4 | propofol 4-phosphoryl-2-(R,S)-fluorobutyrate calcium salt | 4-phosphoryl-2-(R,S)-fluorobutyryl chloride, propofol, DMAP | ESI-MS m/z [M − Ca + H]1− 345.13 |
| G5 | propofol 5-phosphoryl-2-(S)-fluorovalerate zinc salt | 5-phosphoryl-2-(S)-fluoropentanoyl chloride, propofol, DMAP | ESI-MS m/z [M − Zn + H]1− 359.15 |
| G6 | tri[propofol 3-phosphoryl-2-(R,S)-2-monofluoromethylpropionate] dialuminum salt | 3-phosphoryl-2-(R,S)-2-monofluoromethylpropionyl chloride, propofol, DMAP | ESI-MS m/z [M − 2/3Al + H]1− 345.16 |
| G8 | {1-[4-(2,6-diisopropylphenoxy)-4-oxo-2-(R)-trifluoromethyl-butyl]} phosphate monoester dilithium salt | dibenzyl {1-[4-chloro-4-oxo-2-(R)-trifluoromethyl-butyl]}phosphate triester, propofol, DMAP | ESI-MS m/z [M − 2Li + H]1− 411.31 |
| G9 | propofol 4-phosphoryl-2-(R)-fluorobutyrate disodium salt | 4-(dibenzyloxy)phosphoryl-2-(R)-fluorobutyryl chloride, propofol, DMAP | ESI-MS m/z [M − 2Na + H]1− 345.29 |
| G10 | propofol 3-phosphoryl-2-(R,S)-fluoropropionate zinc salt | 3-(dibenzyloxy)phosphoryl-2-(R,S)-fluoropropionyl chloride, propofol, DMAP | ESI-MS m/z [M − Zn + H]1− 331.24 |

The inventors tested the above propofol derivatives, and found that the solubility of all the above compounds was higher than 5 mg/ml in physiological saline (especially compounds E1-E8 and F7, the solubility of which is higher than 20 mg/ml). That is, the propofol derivatives of the present invention have good water solubility.

The inventors provide the following experimental examples to show the surprising and unexpected beneficial effects of the water soluble propofol derivative of the present invention.

Experimental Example 1. In Vitro Dissociation in Blood Plasma

The obtained water soluble propofol derivatives were formulated as 1 mg/ml solutions in physiological saline. 0.1 ml samples were taken from each of the solutions, added respectively to 1 ml of blood plasma of rabbit (taken from New Zealand white rabbits, treated according to conventional methods, anticoagulated with heparin) or 1 ml of blood plasma of rat (taken from live SD rats, processed according to conventional methods, anti coagulated with heparin), homogeneously mixed, and placed in a thermostatic water bath at 37° C. for incubation with time being recorded. Samples were taken at different time points after the experiment began, and 2 ml of acetonitrile was immediately added. The samples were shaken and centrifuged for 5 min (15,000 rpm), and the supernatant was then taken for HPLC analysis. The results are presented as follows:

TABLE 2

The dissociation percent of amino acid-based propofol derivatives of formula E in the blood plasma of rabbit or rat

| | | | | | | | | | Dissociation percent | | |
|---|---|---|---|---|---|---|---|---|---|---|---|
| E | n | $R^9$ | $R^{10}$ | X | Y | C* | A | Plasma | 5 s | 15 s | 30 s |
| E1 | 2 | Me | Me | H | F | R, S | HCl | Rabbit | | 67.5 | 85.5 |
| | | | | | | | | Rat | 75.1 | 83.2 | 96.7 |
| E2 | 2 | Me | Me | H | F | R | HCl | Rabbit | | 97.7 | 100 |
| | | | | | | | | Rat | 100 | | |

TABLE 2-continued

The dissociation percent of amino acid-based propofol derivatives of formula E in the blood plasma of rabbit or rat

| E | n | R$^9$ | R$^{10}$ | X | Y | C* | A | Plasma | Dissociation percent 5 s | 15 s | 30 s |
|---|---|---|---|---|---|---|---|---|---|---|---|
| E3 | 2 | Me | Me | H | CF$_3$ | R | HCl | Rabbit | | 51.7 | 67.2 |
| | | | | | | | | Rat | 77.5 | | |
| E4 | 2 | Me | Et | H | F | R, S | HCl | Rabbit | | 58.3 | 70.4 |
| | | | | | | | | Rat | 70.2 | | |
| E5 | 3 | Me | Bn | H | F | S | HCl | Rabbit | | 48.4 | 69.7 |
| | | | | | | | | Rat | 72.3 | 97.3 | |
| E6 | 1 | H | i-Pro | H | CH$_2$F | R, S | MeSO$_3$H | Rabbit | | 27.1 | 44.3 |
| | | | | | | | | Rat | 24.2 | 40.1 | |
| E7 | 2 | —CH$_2$—CH$_2$— | | H | F | S | HCl | Rabbit | | 89.4 | 94.4 |
| | | | | | | | | Rat | 92.3 | | |
| E8 | 2 | —CH$_2$CH$_2$CH$_2$CH$_2$— | | H | F | R | HCl | Rabbit | | 91.1 | 98.2 |
| | | | | | | | | Rat | 95.6 | | |

TABLE 3

The dissociation percent of diacid monoester-based propofol derivatives of formula F in the blood plasma of rabbit or rat

| F | n | M | t | X | Y | C* | Plasma | Dissociation percent 5 s | 15 s | 30 s |
|---|---|---|---|---|---|---|---|---|---|---|
| F1 | 2 | Na | 1 | H | F | R, S | Rabbit | | 47.5 | 75.5 |
| | | | | | | | Rat | 64.1 | 70.2 | 86.7 |
| F2 | 2 | K | 1 | H | F | S | Rabbit | | 73.4 | 94.8 |
| | | | | | | | Rat | 92.3 | | |
| F3 | 2 | Li | 1 | H | CF$_3$ | R | Rabbit | | 28.4 | 47.9 |
| | | | | | | | Rat | 47.4 | | |
| F4 | 5 | Ca | 2 | H | F | R, S | Rabbit | | 48.3 | 61.7 |
| | | | | | | | Rat | 63.8 | | |
| F5 | 3 | Zn | 2 | H | F | S | Rabbit | | 34.9 | 58.8 |
| | | | | | | | Rat | 63.2 | 80.3 | |
| F6 | 6 | Al | 3 | H | CH$_2$F | R, S | Rabbit | | 37.1 | 58.3 |
| | | | | | | | Rat | 34.2 | 55.7 | |
| F7 | 1 | Na | 1 | H | F | R | Rabbit | | 46.3 | 72.8 |
| | | | | | | | Rat | 58.8 | 71.3 | 85.4 |
| F8 | 0 | Na | 1 | H | F | S | Rabbit | | 41.2 | 70.4 |
| | | | | | | | Rat | 55.5 | 69.3 | 83.3 |

TABLE 4

The dissociation percent of organic phosphate-based propofol derivatives of formula G in the blood plasma of rabbit or rat

| G | n | q | M | t | X | Y | C* | Plasma | Dissociation percent 5 S | 15 S | 30 S |
|---|---|---|---|---|---|---|---|---|---|---|---|
| G1 | 2 | 1 | K | 1 | H | F | R, S | Rabbit | | 43.7 | 68.7 |
| | | | | | | | | Rat | 54.1 | 67.4 | 86.9 |
| G2 | 2 | 1 | Na | 1 | H | F | S | Rabbit | | 37.2 | 54.3 |
| | | | | | | | | Rat | 48.5 | 69.7 | |
| G3 | 2 | 1 | Li | 1 | H | CF$_3$ | R | Rabbit | | 21.7 | 43.6 |
| | | | | | | | | Rat | 38.7 | | |
| G4 | 2 | 0 | Ca | 2 | H | F | R, S | Rabbit | | 43.3 | 54.8 |
| | | | | | | | | Rat | 47.2 | | |
| G5 | 3 | 0 | Zn | 2 | H | F | S | Rabbit | | 33.8 | 56.3 |
| | | | | | | | | Rat | 32.9 | 57.6 | |
| G6 | 1 | 0 | Al | 3 | H | CH$_2$F | R, S | Rabbit | | 27.1 | 44.3 |
| | | | | | | | | Rat | 22.1 | 39.7 | |

Experimental Example 2. Pharmacodynamic Test of the Water Soluble Propofol Derivatives 2.1. Test Samples and Administration An appropriate amount of test compounds (E2, F1, F7, and G2) were weighed out, and a certain amount of physiological saline was added thereto, so as to form 3 mg/ml or 6 mg/ml solutions, which were then sonicated to dissolve the compounds. Test samples for the experiment on rabbit were formulated to have corresponding concentrations based on the results from a preliminary test. As a control, a fat emulsion injection of propofol (commercially available, 10 mg/ml) was diluted to 3 mg/ml with physiological saline. Rats and mice were administered with samples having a fixed concentration of drugs, while the volume of administration altered according to actual situation. The volume of administration to rabbits was 1 mL/kg body weight.

2.2. ED$_{50}$ and LD$_{50}$ Tests of Compounds

ED$_{50}$ and LD$_{50}$ values concerning anesthesia were determined using a sequential method. Healthy KM mice (male), SD rats (male) and New Zealand White rabbits were used for test. For rats and mice, the compounds were administered by injection at a constant rate via caudal vein for 10 seconds. For rabbits, the compounds were administered by injection at a constant rate via ear vein for 30 seconds. Before the test, a preliminary test was conducted to determine an approximate dosage (volume of administration) that leads to anesthetization (or death) of animals, which was set as the middle dosage in the formal test. 2-3 Dosage groups were set above and below the middle dosage group with an interval of 0.8. The disappearance of righting reflex or death was used as indicators of pharmacological efficacy or toxicity, respectively. The formal test began with the administration of the middle dosage. If animals were anesthetized, a lower dosage was administered; if animals were not anesthetized, a higher dosage was administered, until the cycle was repeated for 3-4 times. LD$_{50}$ and ED$_{50}$ were calculated by a sequential method aot425 software. TI was calculated according to the following equation: TI=LD$_{50}$/ED$_{50}$.

Test Results 2.2.1. Test results of LD$_{50}$/ED$_{50}$ and TI index of the compounds in rats/mice. The test results are shown in following Table 5:

TABLE 5

Test results of $LD_{50}/ED_{50}$ and TI index of the compounds in rats/mice (n = 10-20)

| Compd. No. and Concentration | Mouse | | Rat | | TI | |
|---|---|---|---|---|---|---|
| | $LD_{50}$ (mg/kg) | $ED_{50}$ (mg/kg) | $LD_{50}$ (mg/kg) | $ED_{50}$ (mg/kg) | Mouse | Rat |
| E2 (3 mg/ml) | 71.8 (51.1-150)* | 17.9 (13.7-21.9)* | 37.5 (30.9-40.9) | 9.8 (8.3-11.7) | 4* | 3.8 |
| | 46.9 (41.3-59.9) | 15.4 (11.7-21.7) | | | 3 | |
| E2 (6 mg/ml) | 55.1 (42.4-67.8)* | 15.2 (7.4-20.6)* | 30.7 (28.3-36.2) | 10.1 (9.3-12.3) | 3.6* | 3.1 |
| | 48.0 (43.6-51.2) | 13.0 (11.8-15.7) | | | 3.7 | |
| F1 (3 mg/ml) | 63.4 (48.7-138.4)* | 20.8 (15.6-22.7)* | 44.1 (39.3-47.2) | 14.6 (10.2-16.7) | 3* | 3.0 |
| | 52.3 (42.5-56.4) | 18.6 (15.4-21.8) | | | 2.8 | |
| F1 (6 mg/ml) | 49.7 (33.7-64.2)* | 18.2 (15.3-23.4)* | 42.3 (39.6-44.2) | 11.3 (9.5-13.4) | 2.7* | 3.7 |
| | 55.4 (51.8-58.3) | 16.7 (14.4-18.8) | | | 3.3 | |
| F7 (3 mg/ml) | 59.8 (50.3-135.9)* | 21.4 (17.1-23.8)* | 47.4 (41.5-51.7) | 15.7 (12.1-18.9) | 2.8* | 3.0 |
| | 51.6 (41.2-57.4) | 19.2 (17.3-22.8) | | | 2.6 | |
| F7 (6 mg/ml) | 51.2 (35.3-65.8)* | 20.7 (15.9-26.7)* | 44.4 (40.7-47.2) | 12.5 (10.3-14.8) | 2.4* | 3.5 |
| | 56.6 (53.4-60.4) | 18.1 (14.9-21.3) | | | 3.1 | |
| G2 (3 mg/ml) | 65.7 (49.4-141.2)* | 23.7 (15.6-32.3)* | 55.4 (52.7-57.1) | 16.7 (14.2-18.3) | 2.8* | 3.3 |
| | 60.4 (56.4-62.3) | 19.8 (18.4-21.5) | | | 3.0 | |
| G2 (6 mg/ml) | 48.7 (38.7-67.2)* | 25.6 (14.3-29.8)* | 60.1 (58.2-62.4) | 21.1 (19.2-23.4) | 1.9* | 2.8 |
| | 53.6 (60.2-66.3) | 22.8 (17.8-22.3) | | | 2.3 | |
| Propofol (3 mg/ml) | 38.4 (29.2-54.3) | 7.9 (6.5-9.6) | 21.5 (19.2-24) | 3.91 (0.6-5.5) | 4.9 | 5.5 |
| Propofol (6 mg/ml) | 42.9 (38.4-48.0) | 11.3 (10.1-12.6) | 17.4 (16.1-18.4) | 3.5 (0.4-4.3) | 3.8 | 4.9 |

Values marked with * are data from the first test. The remaining data are from the confirmation test.

Conclusion: the water soluble propofol derivatives of the present invention achieved an anesthetic effect in both rats and mice.

2.2.1. Test results of $LD_{50}/ED_{50}$ and TI index of the compounds in rabbits. The test results are shown in following Table 6:

TABLE 6

Test results of $LD_{50}/ED_{50}$ and TI index of the compounds in rabbits

| Compd. No. | $LD_{50}$ (mg/kg) | $ED_{50}$ (mg/kg) | TI index |
|---|---|---|---|
| E2 | 28 (23.0-34.2) | 8 (5.7-10.5) | 3.5 |
| F1 | 34.4 (32.1-36.5) | 12.2 (10.6-14.6) | 2.8 |
| F7 | 36.7 (33.8-39.4) | 13.9 (11.1-16.8) | 2.6 |
| G2 | 38.7 (35.1-41.3) | 14.7 (12.6-19.1) | 2.6 |

Conclusion: the water soluble propofol derivatives of the present invention achieved an anesthetic effect in rabbits.

2.3. Determination of Latent Period and Persistent Period of Anesthesia of the Compounds in Mice Kunming mice (male, 5 per group) were administered with test compounds by injection at a constant rate via tail intravenous for 10 seconds. The periods during which the righting reflex of mice disappeared (latent period) and recovered (persistent period) were recorded.

TABLE 7

Test results of latent period and persistent period for anesthesia of compounds in mice (mice, mg/kg, n = 5)

| Compd. No. | Dosage (mg/kg) | Latent Period (s) | Persistent period (s) |
|---|---|---|---|
| E2 (3 mg/ml) | 36 (2 * $ED_{50}$) | 14.6 ± 0.9 | 383.6 ± 242.1 |
| E2 (6 mg/ml) | 30 (2 * $ED_{50}$) | 14.2 ± 1.9 | 543 ± 231 |
| F1 (3 mg/ml) | 42 (2 * $ED_{50}$) | 18.6 ± 0.7 | 349.7 ± 229.4 |
| F1 (6 mg/ml) | 36 (2 * $ED_{50}$) | 15.2 ± 1.4 | 523 ± 248 |
| F7 (3 mg/ml) | 43 (2 * $ED_{50}$) | 20.2 ± 0.6 | 335.5 ± 218.1 |
| F7 (6 mg/ml) | 41 (2 * $ED_{50}$) | 16.2 ± 2.2 | 517 ± 231 |
| G2 (3 mg/ml) | 47 (2 * $ED_{50}$) | 16.3 ± 0.8 | 383.6 ± 242.1 |
| G2 (6 mg/ml) | 51 (2 * $ED_{50}$) | 15.7 ± 2.3 | 571 ± 173 |
| Propofol (3 mg/ml) | 25 (2 * $ED_{50}$) | 8.4 ± 1.1 | 324.8 ± 98.9 |

Conclusion: the water soluble propofol derivatives of the present invention achieve a rapid onset of anesthesia and a short persistent period.

As demonstrated by the above test results, the water soluble propofol derivatives of the present invention have good water solubility, can be formulated as suitable water soluble preparations, can be easily dissociated in vivo to release propofol, have low toxicity in vivo, and is very suitable as prodrugs of propofol.

What is claimed is:

1. A water soluble propofol derivative of general formula (I):

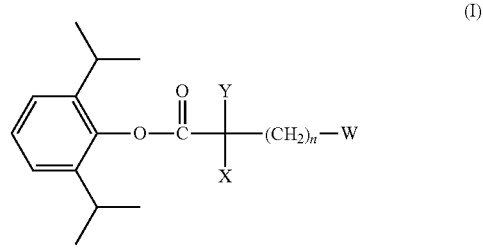

wherein,
X is H or F;
Y is F or alkyl substituted with one or more F;
n is 1, 2, 3, 4, 5 or 6;

W is $W^1$ or $W^2$;

$W^1$ is $NR^1R^2 \cdot A$ or

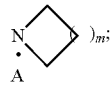

$R^1$, $R^2$ are each independently H, alkyl optionally substituted with phenyl, or cycloalkyl;

m is 0, 1, 2 or 3;

A is a pharmaceutically acceptable acid;

$W^2$ is $COOM_{1/t}$ or $OPO_3(M)_{2/t}$ or $PO_3(M)_{2/t}$;

M is a metal ion, an ammonium ion or a basic amino acid cation which can form a salt with an acid radical; and t is the charge number of M.

2. The water soluble propofol derivative according to claim 1, characterized in that the water soluble propofol derivative has the following general formula (I-1):

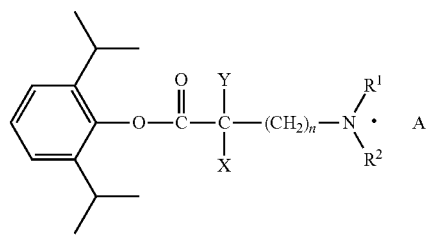

wherein,

X, Y, n, $R^1$, $R^2$ and A are as defined in claim 1.

3. The water soluble propofol derivative according to claim 1, characterized in that the water soluble propofol derivative has the following general formula (I-2):

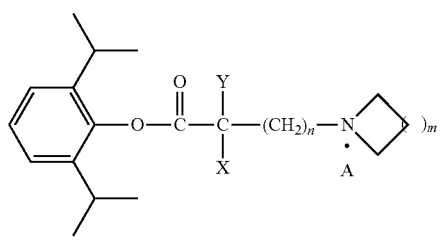

wherein,

X, Y, n, m and A are as defined in claim 1.

4. The water soluble propofol derivative according to claim 1, characterized in that the water soluble propofol derivative has the following general formula (I-3):

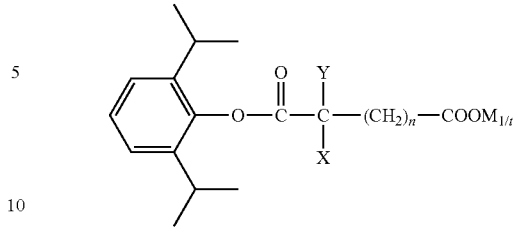

wherein,

X, Y, n, M and t are as defined in claim 1.

5. The water soluble propofol derivative according to claim 1, characterized in that the water soluble propofol derivative has the following general formula (I-4):

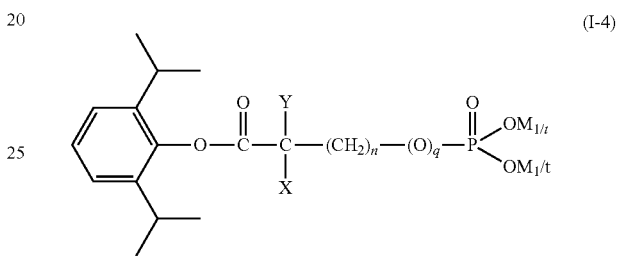

wherein,

X, Y, n, M and t are as defined in claim 1;

q is 0 or 1.

6. The water soluble propofol derivative according to claim 1, characterized in that the metal ion is an alkali metal ion, an alkaline earth metal ion or a trivalent metal ion.

7. The water soluble propofol derivative according to claim 6, characterized in that the metal ion is a lithium ion, a sodium ion or a potassium ion.

8. The water soluble propofol derivative according to claim 6, characterized in that the alkaline earth metal ion is a magnesium ion, a zinc ion or a calcium ion.

9. The water soluble propofol derivative according to claim 6, characterized in that the trivalent metal ion is an aluminum ion.

10. The water soluble propofol derivative according to claim 1, characterized in that the ammonium ion is $(NR^3R^4R^5R^6)^+$ or

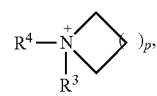

wherein, $R^3$, $R^4$, $R^5$, $R^6$ are each independently H, alkyl optionally substituted with phenyl, or cycloalkyl and;

p is 0, 1, 2 or 3.

11. The water soluble propofol derivative according to claim 10, characterized in that the alkyl is $C_{1-6}$ alkyl.

12. The water soluble propofol derivative according to claim 11, characterized in that the $C_{1-6}$ alkyl is methyl, ethyl, propyl, isopropyl, butyl or isobutyl.

13. The water soluble propofol derivative according to claim 10, characterized in that the cycloalkyl is $C_{3-6}$ cycloalkyl.

14. The water soluble propofol derivative according to claim 13, characterized in that the $C_{3-6}$ cycloalkyl is cyclopropyl, cyclobutyl, cyclopentyl or cyclohexyl.

15. The water soluble propofol derivative according to claim 10, characterized in that $R^3$, $R^4$, $R^5$ and $R^6$ are each independently H, methyl, ethyl, propyl, isopropyl, butyl, isobutyl, benzyl, cyclopropyl, cyclobutyl, cyclopentyl or cyclohexyl.

16. The water soluble propofol derivative according to claim 15, characterized in that $R^3$ and $R^4$ are each independently H, methyl or ethyl.

17. The water soluble propofol derivative according to claim 1, characterized in that the basic amino acid cation is arginine+H$^+$, lysine+H$^+$ or histidine+H$^+$.

18. The water soluble propofol derivative according to claim 1, characterized in that the alkyl is $C_{1-6}$ alkyl.

19. The water soluble propofol derivative according to claim 18, characterized in that the $C_{1-6}$ alkyl is methyl, ethyl, propyl, isopropyl, butyl or isobutyl.

20. The water soluble propofol derivative according to claim 1, characterized in that Y is F, $CF_3$ or $CHF_2$.

21. The water soluble propofol derivative according to claim 1, characterized in that the cycloalkyl is $C_{3-6}$ cycloalkyl.

22. The water soluble propofol derivative according to claim 21, characterized in that $C_{3-6}$ cycloalkyl is cyclopropyl, cyclobutyl, cyclopentyl or cyclohexyl.

23. The water soluble propofol derivative according to claim 1, characterized in that $R^1$ and $R^2$ are each independently H, methyl, ethyl, propyl, isopropyl, butyl, isobutyl, benzyl, cyclopropyl, cyclobutyl, cyclopentyl or cyclohexyl.

24. The water soluble propofol derivative according to claim 1, characterized in that $R^1$ and $R^2$ are not H at the same time.

25. The water soluble propofol derivative according to claim 1, characterized in that the pharmaceutically acceptable acid is hydrochloric acid, hydrobromic acid, sulfuric acid, phosphoric acid, carbonic acid, acetic acid, propionic acid, methanesulfonic acid, lactic acid, benzensulfonic acid, p-toluene sulfonic acid, succinic acid, maleic acid, fumaric acid, tartaric acid, citric acid or malic acid.

26. The water soluble propofol derivative according to claim 1, characterized in that when X and Y are different, the carbon atom to which both X and Y are attached is in a single R configuration, in a single S configuration, or in both R and S configurations.

27. The water soluble propofol derivative according to claim 1, which is selected from the group consisting of:
propofol 4-(N,N-dimethyl)amino-2-(R,S)-fluorobutyrate hydrochloride;
propofol 4-(N,N-dimethyl)amino-2-(R)-fluorobutyrate hydrochloride;
propofol 3-N-isopropylamino-2-(R,S)-fluoropropionate hydrochloride;
propofol-2-(R,S)-fluoropentanoate monoester sodium salt;
propofol-2-(R,S)-fluorobutyrate monoester sodium salt;
propofol-2-(R)-fluoropropionate monoester sodium salt;
{1-[3-(2,6-diisopropylphenoxy)-3-oxo-2-(R)-fluoropropyl]} phosphate monoester dipotassium salt;
propofol 4-(N,N-dimethyl)amino-2-(R)-fluorobutyrate hydrochloride;
propofol 4-(N,N-dimethyl)amino-2-(R)-2-trifluoromethylbutyrate hydrochloride;
propofol 4-(N-methyl-N-ethyl)amino-2-(R,S)-2-fluorobutyrate hydrochloride;
propofol 5-(N-methyl-N-benzyl)amino-2-(S)-2-fluorovalerate hydrochloride;
propofol 3-(N-isopropyl)amino-2-(R,S)-2-monofluoromethylpropionate methanesulfonate;
propofol 4-(aziridin-1-yl)-2-(S)-2-fluorobutyrate hydrochloride;
propofol 4-(pyrrolidin-1-yl)-2-(R)-2-fluorobutyrate hydrochloride;
propofol 3-(N,N-diethyl)amino-2-(R,S)-fluoropropionate hydrochloride;
propofol 4-(N-methyl-N-benzyl)amino-2-(R,S)-trifluoromethylbutyrate hydrochloride;
propofol 4-(N-cyclopropyl-N-methyl)amino-2-(R)-difluoromethylbutyrate hydrochloride;
propofol 3-(pyrrolidin-1-yl)-2-(S)-trifluoromethylpropionate hydrochloride;
propofol δ-(N,N-dimethyl)amino-2-(R)-fluorovalerate hydrochloride;
propofol 3-N-methyl-N-cyclohexylamino-2-(R,S)-fluoropropionate hydrochloride;
propofol 4-(N-methyl-N-isopropyl)amino-2-(R,S)-fluorobutyrate methanesulfonate;
propofol 5-N-cyclopentylamino-2,2-difluorovalerate hydrochloride;
propofol 4-(N,N-dimethyl)amino-2-(R)-trifluoromethylbutyrate hydrochloride;
propofol 4-N-methyl-N-benzylamino-2-(R)-fluorobutyrate hydrochloride;
propofol 4-carboxyl-2-(S)-fluorovalerate potassium salt;
propofol 4-carboxyl-2-(R)-2-trifluoromethylvalerate lithium salt;
di[propofol 7-carboxyl-2-(R,S)-fluorocaprylate] calcium salt;
di[propofol 5-carboxyl-2-(S)-fluorohexanoate] zinc salt;
tri[propofol 8-carboxyl-2-(R,S)-monofluoromethylpelargonate] aluminum salt;
propofol 4-carboxyl-2-(S)-trifluoromethylbutyrate ammonium salt;
propofol 4-carboxyl-2-(R,S)-difluoromethylvalerate potassium salt;
{1-[4-(2,6-diisopropylphenoxy)-4-oxo-3-(R,S)-3-fluoro-1-butyl]} phosphate monoester dipotassium salt;
{1-[4-(2,6-diisopropylphenoxy)-4-oxo-3-(S)-3-fluoro-1-butyl]} phosphate monoester disodium salt;
{1-[4-(2,6-diisopropylphenoxy)-4-oxo-3-(R)-3-trifluoromethyl-1-butyl]} phosphate monoester dilithium salt;
propofol 4-phosphoryl-2-(R,S)-fluorobutyrate calcium salt;
propofol 5-phosphoryl-2-(S)-fluorovalerate zinc salt;
tri[propofol 3-phosphoryl-2-(R,S)-2-monofluoromethylpropionate] dialuminum salt;
{1-[4-(2,6-diisopropylphenoxy)-4-oxo-2-(R)-trifluoromethylbutyl]} phosphate monoester dilithium salt;
propofol 4-phosphoryl-2-(R)-fluorobutyrate disodium salt;
propofol 3-phosphoryl-2-(R,S)-fluoropropionate zinc salt.

28. The water soluble propofol derivative according to claim 1 formulated as an intravenous anesthetic.

29. An anesthetization method, comprising intravenous administration of the water soluble propofol derivative according to claim 1 to a patient.

* * * * *